US009045511B2

(12) United States Patent
Hierso et al.

(10) Patent No.: US 9,045,511 B2
(45) Date of Patent: Jun. 2, 2015

(54) SUPPORTED LIGANDS HAVING A HIGH LOCAL DENSITY OF COORDINATING ATOMS

(75) Inventors: Jean-Cyrille Hierso, Dijon (FR); Matthieu Beauperin, Dijon (FR); Philippe Meunier, Bellefond (FR)

(73) Assignees: CENTRE NATIONAL DE LA RECHERCHE SCIENTIFIQUE, Paris (FR); UNIVERSITE DE BOURGOGNE, Dijon Cedex (FR)

( * ) Notice: Subject to any disclaimer, the term of this patent is extended or adjusted under 35 U.S.C. 154(b) by 152 days.

(21) Appl. No.: 13/807,645

(22) PCT Filed: Jun. 24, 2011

(86) PCT No.: PCT/IB2011/052794

§ 371 (c)(1), (2), (4) Date: Dec. 28, 2012

(87) PCT Pub. No.: WO2012/001601

PCT Pub. Date: Jan. 5, 2012

(65) Prior Publication Data

US 2013/0158219 A1 Jun. 20, 2013

(30) Foreign Application Priority Data

Jun. 29, 2010 (FR) .................................... 10 02705

(51) Int. Cl.

*C07F 17/02* (2006.01)
*C07F 15/02* (2006.01)
*C07D 319/06* (2006.01)

(52) U.S. Cl.

CPC ............. *C07F 15/02* (2013.01); *C07D 319/06* (2013.01); *C07F 17/02* (2013.01)

(58) Field of Classification Search

CPC ........ C07F 15/02; C07F 17/02; C07D 319/06
USPC ........ 556/11, 22; 549/206, 221, 369; 568/316
See application file for complete search history.

(56) References Cited

FOREIGN PATENT DOCUMENTS

| | | |
|---|---|---|
| SU | 709 625 | 1/1980 |
| WO | WO 2006/114438 | 11/2006 |
| WO | WO 2006/117369 | 11/2006 |

OTHER PUBLICATIONS

Ivanov V. V., Hierso J.-C., Amardeil R., Meunier P.: "General Route to Dissymetric Heteroannular-Functionalized Ferrocyenyl 1,2-Diphosphines: Selective Synthesis and Characterization of a New Class of Tri- and Tetrasubstituted Ferrocenyl Compounds", Organometallics, vol. 25, 2006, pp. 989-995.

International Search Report for PCT/IB2011/052794 mailed Oct. 25, 2011.

*Primary Examiner* — Porfirio Nazario Gonzalez
(74) *Attorney, Agent, or Firm* — Hunton & Williams LLP

(57) ABSTRACT

The invention relates to compounds, in particular phosphinic ligands of metal complexes, as well as to metal complexes including said ligands and to supported catalysts including said metal complexes or said compounds. The invention also relates to methods for synthesizing said compounds, to complexes, and to supported catalysts, as well as to intermediate products used in said synthesis methods. The invention further relates to the uses of said compounds. The compounds of the invention are ferrocene compounds which have been functionalized so as to be capable of being heterogenized. The invention can be used in particular in the field of heterogeneous catalysis.

31 Claims, No Drawings

SUPPORTED LIGANDS HAVING A HIGH LOCAL DENSITY OF COORDINATING ATOMS

CROSS-REFERENCE TO RELATED APPLICATIONS

This is the U.S. National Stage application of International Patent Application No. PCT/IB2011/052794, filed Jun. 24, 2011, which claims priority to FR 10 02705, filed Jun. 29, 2010, the disclosures of each of which are hereby incorporated by reference in their entirety.

The invention relates to compounds which are, more particularly, phosphine ligands of metal complexes, as well as to metal complexes comprising these ligands, and to supported catalysts comprising these metal complexes or these compounds.

It also relates to processes for the synthesis of these compounds, complexes, and supported catalysts, and to intermediate products used in these synthesis processes.

It further relates to the use of the compounds of the invention for the manufacture of a supported catalyst, or of a complex according to the invention for the manufacture, also, of a supported catalyst.

Lastly, it relates to processes for catalytic coupling of nucleophilic and electrophilic compounds, based on the use of these complexes and supported catalysts.

Homogeneous catalysis at high dilution is a process which considerably limits the amount of metal and ligand that are used in catalytic reactions. This is a cleaner synthesis process, which has a high potential in the pharmaceutical industry, as described by V. Farina (*Adv. Synth. Catal.* 2004, 346, 1553-1582).

There is a known class of catalysts which have proved their efficiency in homogeneous catalysis at high dilution (from 0.1 to 0.0001 mol % of catalyst, relative to the number of moles of limiting reactant).

These catalysts are composed of a ligand, which is a ferrocenyl polyphosphine compound with controlled conformation (see M. Beaupérin et al. in *Eur. J. Inorg. Chem.* 2007, 3767-3780), complexed with a catalytic metal.

The advantageous properties of this class of catalysts are due to the use of ferrocenyl phosphine ligands having controlled conformation.

These ligands are more particularly the following, of formula (a) to (l):

Formula (a)

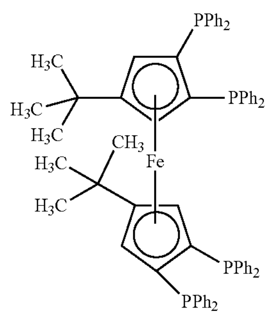

-continued

Formula (b)

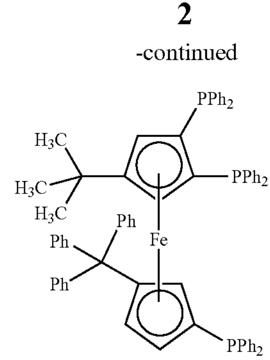

Formula (c)

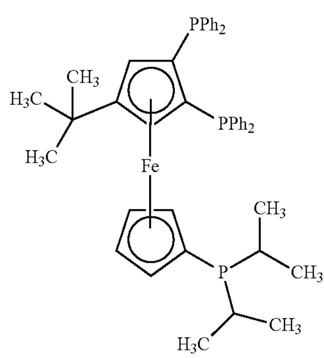

Formula (d)

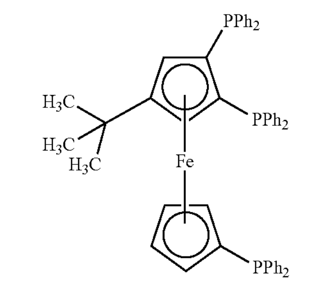

Formula (e)

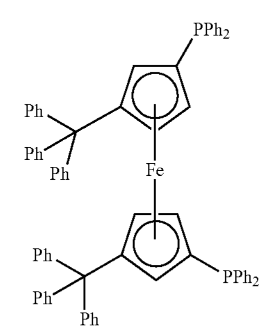

Formula (f)

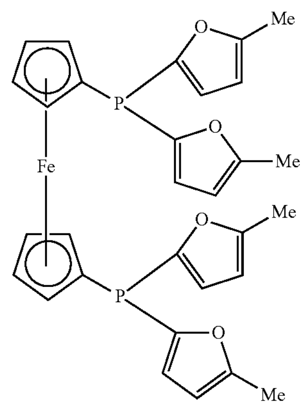

-continued

Formula (g)

Formula (h)

Formula (i)

Formula (j)

Formula (k)

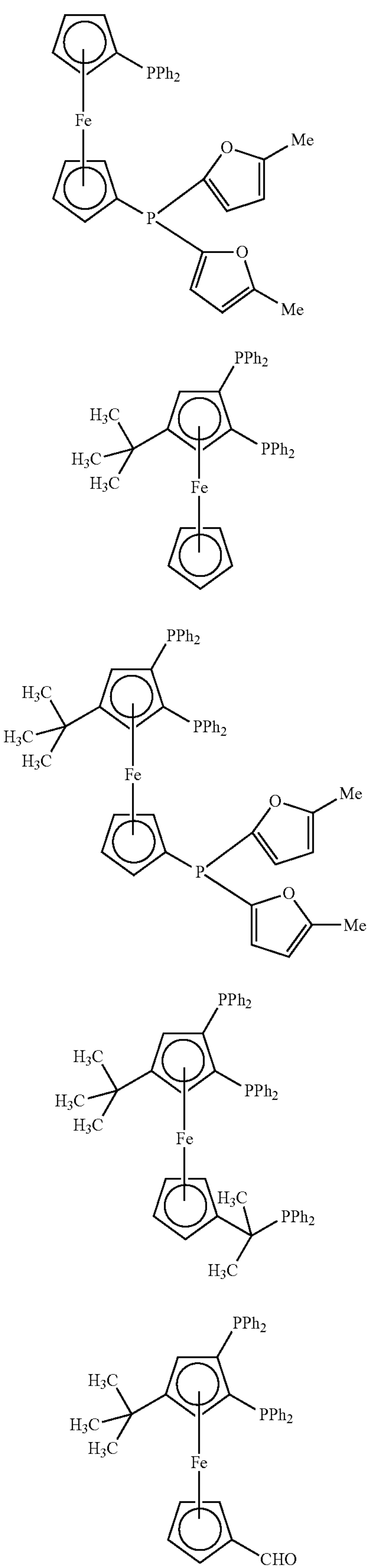

-continued

Formula (l)

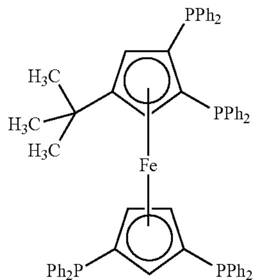

The syntheses and the properties in catalysis at high dilution of these ligands are described more particularly in: J.-C. Hierso et al. *Organometallics* 2003, 22, 4490-4499; J.-C. Hierso et al. *Org. Lett.* 2004, 6, 3473-3476; J.-C. Hierso et al. *Tetrahedron* 2005, 61, 9759-9766; A. Fihri et al. *Adv. Synth. Catal.* 2005, 347, 1198-1202, V. V. Ivanov et al. *Organometallics* 2006, 25, 989-995, R. V. Samliy et al. *Organometallics* 2009, 28, 3152-3160, J. Roger et al. *ChemCatChem* 2010, 2, 296-305.

These ligands, and more particularly the ligand of formula (a), which is a ligand containing four phosphine groups, have a controlled conformation, owing to the tert-butyl (t-Bu) group or groups, which controls or control the implanting of the phosphoruses on the cyclopentadienyl ring, and which produces or produce both an excellent accessibility and a great mutual spatial proximity of the electron-donating phosphorus atoms which are able to interact in synergy with a metal, and more particularly the catalytic metal (as demonstrated in J.-C. Hierso et al. *J. Am. Chem. Soc.,* 2004, 126, 11077-11087; J.-C. Hierso et al. *Organometallics* 2003, 22, 4490-4499; D. Evrard et al. *Organometallics* 2008, 27, 2643-2653).

However, these catalysts can be used only in homogeneous catalysis.

However, with the goal of cleaner chemistry and with the goal of being able to use a catalyst again, by recycling it, it is preferable to use a heterogeneously catalyzed reaction.

For this purpose, certain catalysts used industrially and in academic research are said to be "heterogeneized" (or supported) catalysts, which means that they are immobilized or grafted on a (soluble or insoluble) solid support, or are copolymerized to give a (soluble or insoluble) coordinating resin.

However, the ferrocenyl polyphosphine ligands described above have never, to date, been able to be "heterogeneized", and this is particularly true of the compound of formula (a).

The reason is that the available sites on the pentadiene rings of this ferrocenyl polyphosphine ligand are not selectively accessible in such a way as to allow their direct functionalization for the purpose of heterogeneizing the ligand; heterogeneization to be carried out by the use of a support which incorporates reactive groups reacting with the functionalizations, or by the immobilization of the ligand via polymerization of the functionalizing groups with one another, or with other monomers.

Moreover, it is essential to preserve the conformation of these ligands, which is due to the t-Bu groups, in particular. On the ferrocenyl polyphosphine ligand, these t-Bu groups are not themselves directly functionalizable.

However, the inventors have now succeeded in creating ferrocenyl polyphosphine ligands which are heterogeneizable—that is, which contain functional groups which are reactive with functional groups of a support or are reactive with one another so as to polymerize, or else are reactive with other monomers, so as to form a copolymer, while preserving the conformation of these ligands, the accessibility of the phosphorus atoms for the catalytic reactive metal, and the proximity of the phosphorus atoms for the multiple stabilization of the catalytic edifice.

The invention is therefore based on the synthesis of ferrocenyl phosphine ligands, and more particularly ferrocenyl di-, tri-, or tetraphosphine ligands, which, in place of the t-Bu groups, comprise chains which carry a reactive functional group bonded to a spacer which is bonded to a "structuring" group which mimics, in particular, the effect of the tert-butyl group, which is itself bonded to the pentadiene rings of the ferrocene molecule.

These compounds have the formula (I) below:

Formula (I)

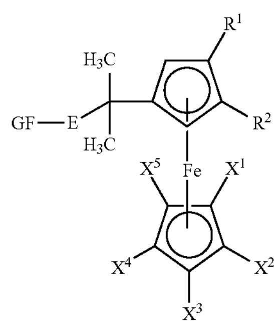

in which:

E is a saturated or unsaturated, linear or branched $C_1$ to $C_{30}$, preferably $C_1$ to $C_{10}$, more preferably $C_1$ to $C_5$ alkyl chain which optionally contains at least one heteroatom, preferably N and/or O, GF is a reactive group selected from the following groups:

vinyl;

formyl;

carbonyl;

acetal;

styrenyl;

alcohol;

silane;

alkoxysilane in which the alkoxy chain is a saturated or unsaturated, linear or branched $C_1$ to $C_{30}$, preferably $C_1$ to $C_{10}$, more preferably $C_1$ to $C_5$ chain optionally containing at least one heteroatom, preferably N and/or O;

silanol;

siloxane;

amine;

imine;

amide;

thiol;

carboxyl, and from the groups of the following formulae:

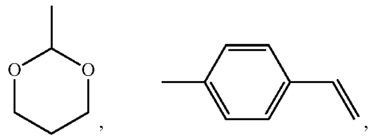

-continued

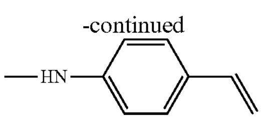

$R^1$ is a phosphine group $P(R^4)_2$, $R^2$ is H or a phosphine group $P(R^6)_2$, $X^1$, $X^2$, $X^3$, and $X^4$ are identical or different and are selected independently of one another from a hydrogen atom, a group $(PR^8)_2$, a group $—C(CH_3)_2—P(R^3)_2$, or an amino group $R^7N(R^5)_2$, $X_5$ is either a group $GF\text{-}E\text{-}C(CH_3)_2—$ in which GF and E are identical to GF and E defined above, or H, or a phosphine group $P(R^{10})_2$ or an amino group $R^{11}N(R^9)_2$, $R^3$, $R^4$, $R^5$, $R^6$, $R^7$, $R^8$, $R^9$, $R^{11}$ and $R^{11}$ are, independently of one another, selected from:

a saturated or unsaturated, linear or branched $C_1$ to $C_{30}$, preferably $C_1$ to $C_{10}$, more preferably $C_5$ to $C_7$ alkyl group containing optionally at least one heteroatom, preferably an N and/or O atom, a $C_3$ to $C_7$ aryl, or cyclic or acyclic aliphatic, group, preferably a $C_1$ to $C_7$ group, optionally containing a heteroatom, preferably an N and/or O atom, and optionally substituted, preferably by a methyl or methoxy group, a halogen atom such as F, Cl, Br or I, or a $CF_3$ group.

$R^3$, $R^4$, $R^5$, $R^6$, $R^8$, $R^9$, and $R^{10}$ are preferably selected from an ethyl (Et), isopropyl (i-Pr), cyclohexyl (Cy), tert-butyl (t-Bu), or phenyl (Ph), or furyl (Fu), group, which are optionally substituted, preferably by at least one methyl or methoxy group, Cl, or $CF_3$, and $R^7$ and $R^{11}$ are a $—CH_2—$ group.

Most preferably, $R^4$ and $R^6$ are a phenyl group, $R^5$ and $R^9$ are both an ethyl group, and $R^7$ and $R^{11}$ are both a $—CH_2—$ group.

In a first preferred embodiment, these ligands, which are also called "compounds" in the present text, have the formula (I-A) below:

Formula (I-A)

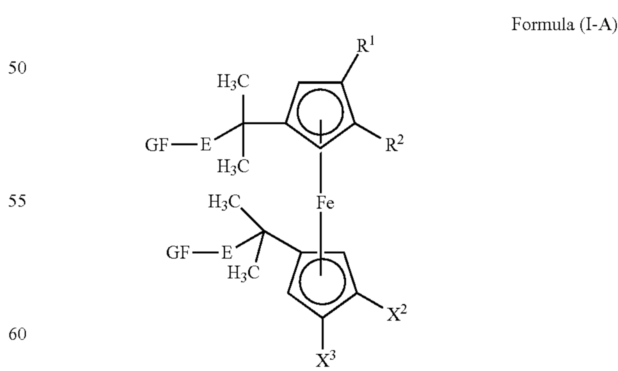

in which $X^5$ is $GF\text{-}E\text{-}C(CH_3)_2—$.

The preferred compounds of formula (I-A) are those in which $X^2{=}X^3{=}P(Ph_2)$ and $X^1{=}X^4{=}H$, and $R^1{=}R^2{=}P(Ph)_2$. These compounds are symmetrical, with $C_2$ symmetry.

Particular preference is given to the compounds of formulae (1) to (8) below:

Formula (1)

Formula (2)

Formula (3)

Formula (4)

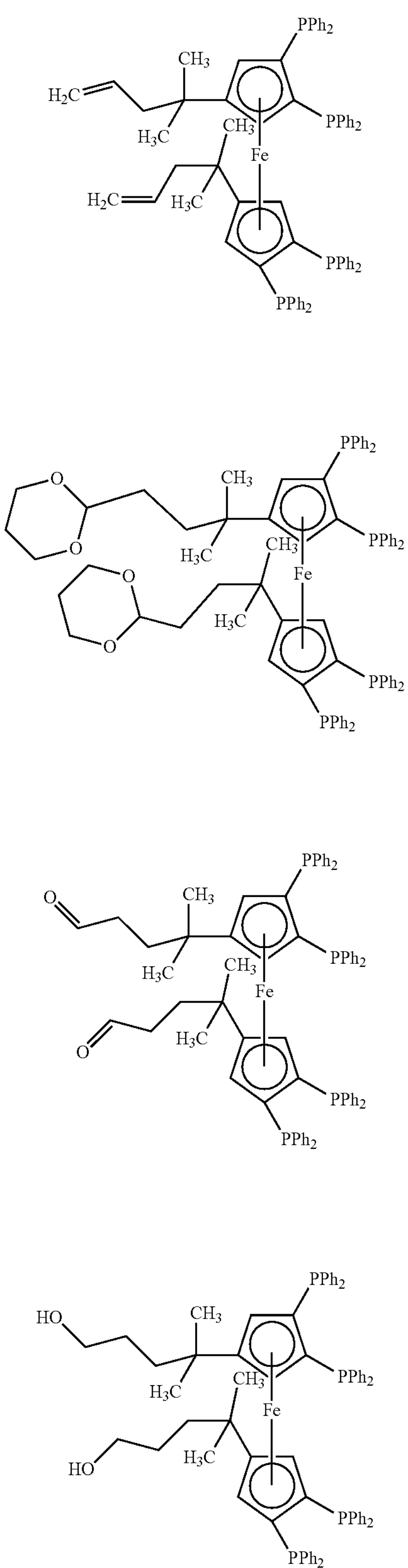

-continued

Formula (5)

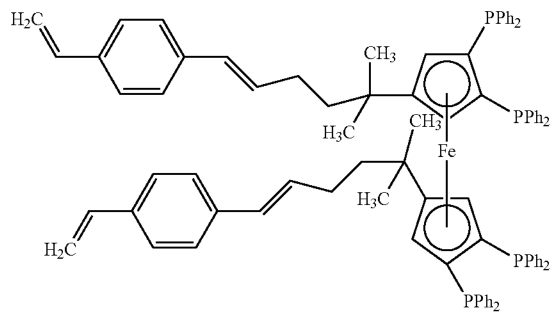

Formula (6)

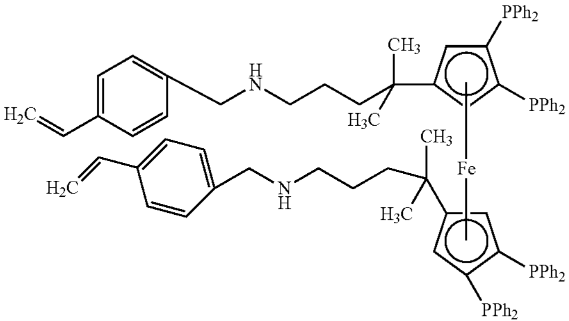

Formula (7)

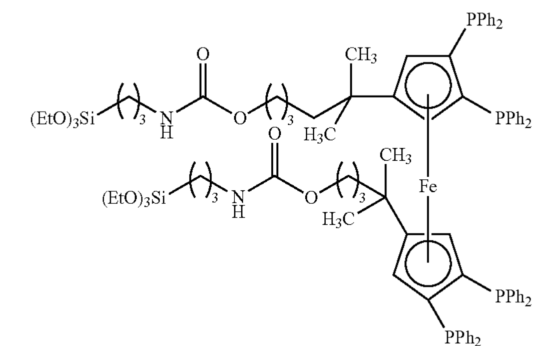

Formula (8)

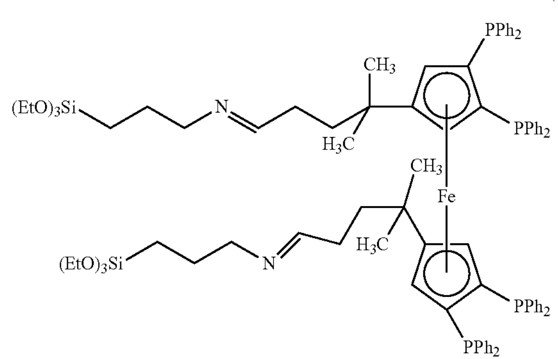

In another preferred embodiment of the compounds of the invention, the compounds have the formula (I) in which $X^5$ is different from GF-E-C$(CH_3)_2$—.

These compounds are asymmetrical.

Particular preference is given to the compounds of formulae (9) to (18) below:

Formula (9)
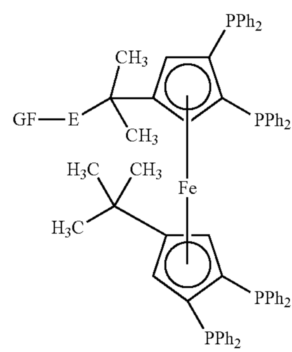
Formula (10)
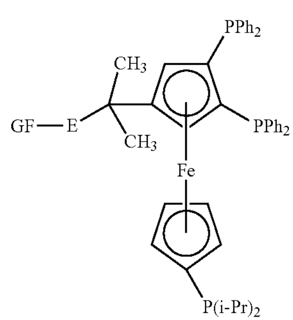
Formula (11)
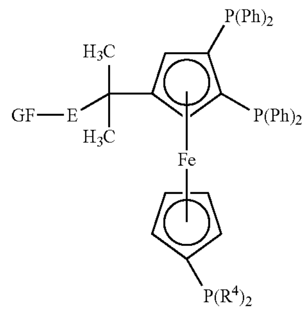
Formula (12)
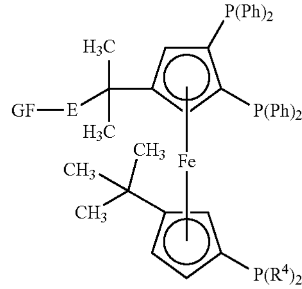
Formula (13)
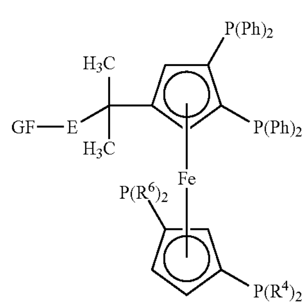
-continued
Formula (14)
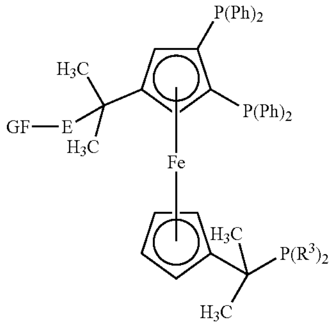
Formula (15)
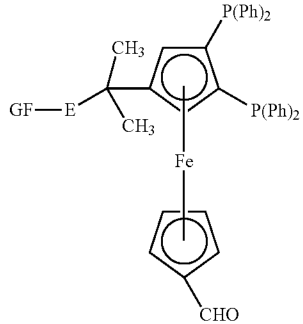
Formula (16)
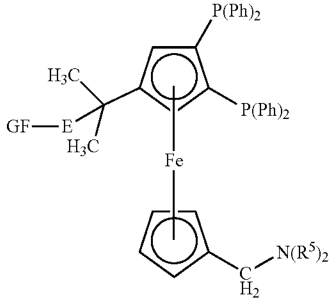
Formula (17)
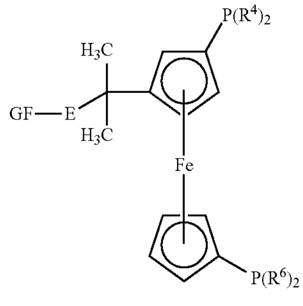
Formula (18)
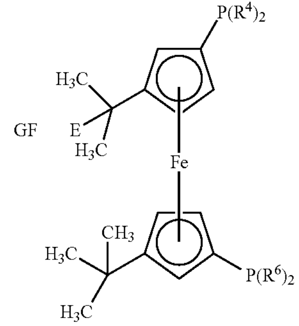

in which:

$R^4$ and $R^6$ denote, independently of one another, an isopropyl, cyclohexyl, tert-butyl, or phenyl, or furyl, group, it being possible for the phenyl or furyl groups optionally to be substituted, preferably by at least one methyl or methoxy group, a halogen atom, or a $CF_3$ group, and $R^5$ denotes either a saturated or unsaturated, linear or branched $C_1$ to $C_{30}$, preferably $C_3$ to $C_{10}$, more preferably $C_3$ to $C_5$ alkyl chain which may contain at least one heteroatom, preferably N and/or O, with $R^5$ preferably denoting an ethyl group, or a $C_5$ to $C_7$ aryl, or cyclic or acyclic aliphatic, group, optionally containing a heteroatom and optionally substituted, preferably by at least one methyl or methoxy group, a halogen atom, or a $CF_3$ group.

Preferably $R^4$ and $R^6$ are both a phenyl group and $R^5$ is an ethyl group.

A halogen atom may be F, Cl, Br, and I.

The halogen atom is preferably Cl or F. The ligand compounds of formulae (1) to (9) are ferrocenyl tetraphosphine ligands.

The ligand compounds of formulae (10) to (14) are ferrocenyl triphosphine ligands.

The ligand compounds of formulae (15) to (18) are ferrocenyl diphosphine ligands.

These are "heterogeneizable" ligands, because the group GF allows them either to be grafted or to be immobilized within a soluble support which is recoverable (depending on the solvent), or an insoluble support.

The conformation of the corresponding known, non-"heterogeneizable" ligands of formulae (a) to (l) is preserved in the functionalized ligands by the GF-E-C($CH_3$)$_2$—groups: that is to say, the compounds of formula (I), and more particularly the compounds of formulae (1) to (9) of the invention, as has been verified by $^1H$, $^{13}C$, and $^{31}P$ multinuclear NMR, and their study by X-ray diffraction, at various stages in their synthesis.

The heterogeneizable ligands of the invention are subsequently immobilized either by grafting on a solid support having reactive functions, or by polymerization of their functional groups with one another or with other monomers.

As a solid support, it is possible to use the solid supports known to the skilled person, such as resins, polymers, silica, alumina, dendrimers, metallic nanoparticles, or latex, mesoporous materials, clays, etc.

The reaction of immobilization on the support takes place by reaction of the GF group of the compounds of formula (I), and more particularly of the compounds of formulae (1) to (18), with reactive groups which are present on or introduced on the support.

Accordingly:

when the group GF is C═O, it will react with the reactive $NH_2$ groups of the support, and conversely, when the group GF is an $NH_2$ group, it will react with the C═O groups of the support;

when the group GF is OH, it will react with the reactive halogen (I, Br, Cl), siloxane ($SiOR_3$), mesylate (Ms), triflate (OTf), or tosylate (OTs) groups of the support, and conversely when the group GF is —CH═$CH_2$, it will react with the reactive halogen (I, Br, Cl) and siloxane (SiOR) groups of the support, and vice versa.

The ligands of the invention may also be immobilized by polymerization of their functional groups. This is the case in particular when these functional groups GF are styrenyl or siloxane groups, such as, for example, the groups GF-1, GF-2, and GF-3:

formula (GF-1)

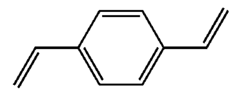

formula (GF-2)

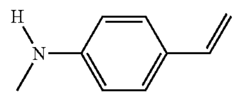

formula (GF-3)

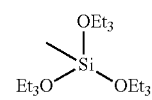

They may be immobilized by copolymerization of their functional groups GF with other organic or inorganic monomers of the same olefinic or alkoxysilane type.

For example, when the group GF has the formula GF-1 or GF-2, it may be copolymerized with the monomers of formula (I-1) below:

Formula (I-1)

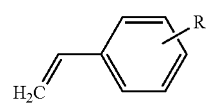

in which R is:

H or at least one linear or branched alkyl group with a saturated or unsaturated $C_1$ to $C_{30}$, preferably $C_1$ to $C_5$, chain, or at least one methoxy group, or at least one halogen such as F, Cl, Br, or I, and preferably F and Cl.

When the group GF is the group GF-3, it may be copolymerized with an alkoxysilane monomer of formula ($SiOR'_3$) in which R' is a linear or branched alkyl group with a saturated or unsaturated $C_1$ to $C_{30}$, preferably $C_1$ to $C_5$, chain.

The ligands of the invention form complexes with a catalytic metal as described, for the corresponding nonheterogeneizable ligands, in J.-C. Hierso et al. *Chem. Soc. Rev.* 2007, 36, 1754-1769. The synthesis of the complexes may take place either before the immobilization of the ligand on the support, or after, according to the following scheme.

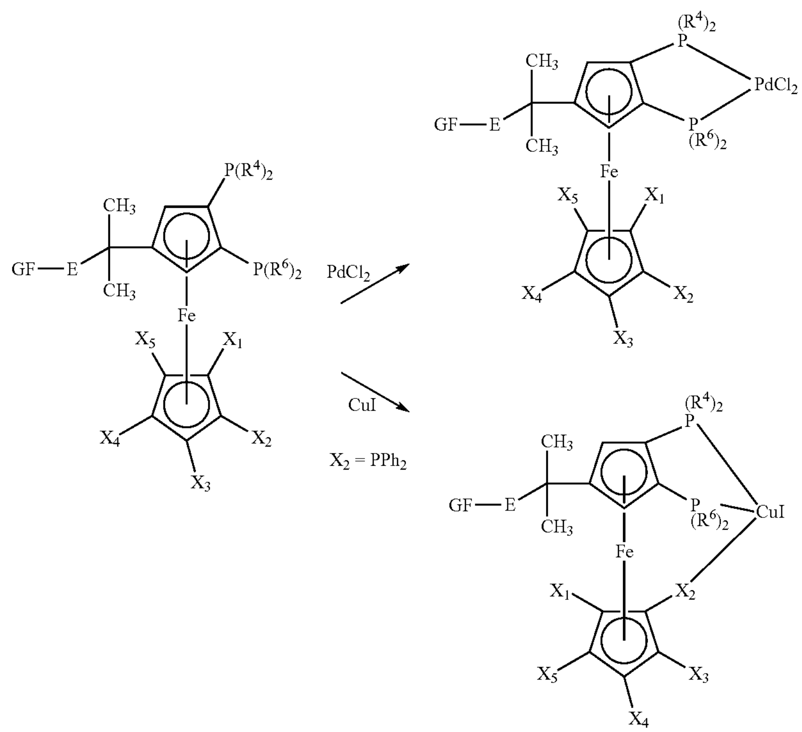

The invention therefore provides complexes comprising a compound of formula (I), preferably a ligand compound of formulae (1) to (18) above, which is complexed with a metal selected from the d transition metals, and more particularly palladium, copper, nickel, platinum, rhodium, iridium, iron, zirconium, titanium, and ruthenium, and also supported complexes comprising a complex according to the invention which is immobilized, as defined above, by grafting of the functional groups GF of the compound of formula (I) with the reactive groups of a support, preferably from ligand compounds of formulae (1) to (18), with the reactive groups of a support, or by polymerization of the functional groups GF of the compounds of formula (I), preferably from ligand compounds of formulae (1) to (18), with one another or with other monomers.

A further subject of the invention is a process for synthesis of a compound of formula (I-A), more particularly having one of the formulae (1) to (8).

This process comprises the following steps:

a) preparation of a cyclopentadienyllithium salt carrying the desired groups E-GF, or carrying a reactive precursor function which leads readily to these desired groups E-GF when the ligand is formed,
b) two successive phosphination/lithiation reactions of the compound obtained in step a), and
c) formation of the desired ferrocene compound by reaction of the compound obtained in step b) with an iron salt.

The invention thus provides a process for synthesis of the compound of formula (1), comprising the following steps:

a) introduction of the functional group GF: —CH═CH$_2$, and of the spacer E: —CH$_2$—, by reaction of 6,6-dimethylfulvene with the organomagnesium compound CH$_2$═CH—CH$_2$—MgCl, to give 1-[2-(2-methyl)pent-4-enyl]cyclopentadiene,
b) lithiation of the product obtained in step a) with n-BuLi, to give 1-[2-[2-methyl]pent-4-enyl]cyclopentadienyllithium,
c) two successive phosphinations of the product obtained in step b) with ClP(Ph)$_2$, between which a step of lithiation with n-BuLi is carried out,
d) treatment of the compound obtained in step c) with n-BuLi, to give 1,2-bis(diphenylphosphino)-4-[2-(2-methyl)pent-4-enyl]cyclopentadienyllithium, and
e) synthesis of the compound of formula (1) by reaction of FeCl$_2$ with the compound obtained in step d).

Another subject of the invention is a process for synthesis of the compound of formula (2), comprising the following steps:

a) reaction of an organomagnesium compound of the formula below:

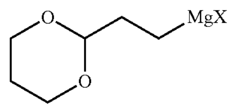

in which X is Br or I with CH$_3$COCl, to give 4-(1,3-dioxan-2-yl)butan-2-one of formula A below:

Formula A

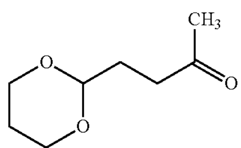

b) reaction of the compound of formula A obtained in step a), with pyrrolidine and the cyclopentadienyllithium (CpLi), to give the 2-[3-(cyclopenta-2,4-dienylidene)butyl]-1,3-dioxane of formula B below:

Formula B

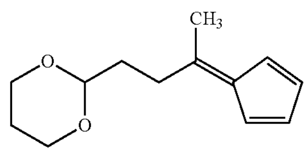

c) lithiation of the compound of formula B with methyllithium (MeLi), to give the compound of formula C below:

Formula C

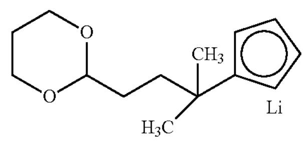

d) two successive phosphinations of the compound of formula C with $ClP(Ph)_2$, with intermediate passage to the lithium salt corresponding to the monophosphination by action of n-BuLi, followed by a treatment with n-BuLi, to give the compound of formula D below:

Formula D

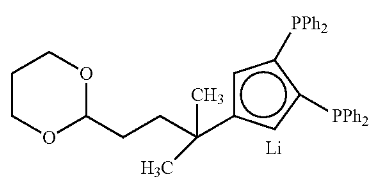

e) formation of the compound of formula (2) below:

Formula (2)

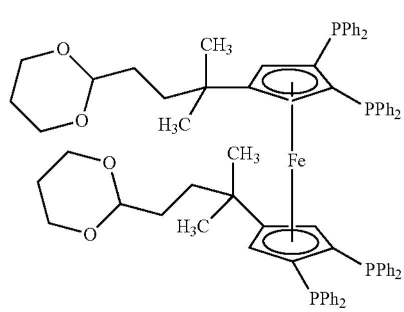

by reaction of the compound of formula D with an iron salt.

It should be noted that in step d), between the two phosphination steps, a lithiation step is implemented on the product obtained after the first phosphination step, with n-BuLi.

The invention also provides a process for synthesis of the compound of formula (3), which comprises the deprotection of the compound of formula (2) under acidic conditions.

On the basis of the compound of formula (3), the invention provides a process for synthesis of the compound of formula (4), which comprises the reduction of this compound of formula (3).

The compound of formula (5) may be manufactured from the compound of formula (3), which is reacted with a compound of formula (I-4) below:

Formula (I-4)

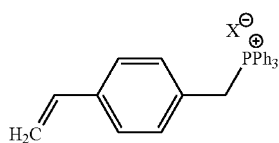

However, the compound of formula (5) may also be prepared by reacting the compound of formula (3) with the compound of formula (I-5) below:

Formula (I-5)

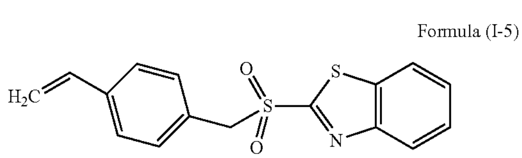 [SMILES: C=Cc1ccc(CS(=O)(=O)c2nc3ccccc3s2)cc1]

As for the compound of formula (6), the invention provides for its synthesis by reaction of the compound of formula (3) with a p-vinylbenzylamine compound of formula (I-2) below:

Formula (I-2)

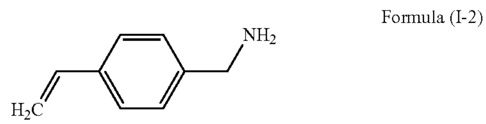

The compound of formula (7) may advantageously be synthesized, according to the invention, by the reaction of the compound of formula (4) with an alkoxysilane compound of formula (I-6) below:

Formula (I-6)

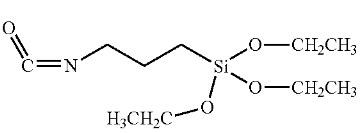

The compound of formula (8) may be synthesized by the reaction of the compound of formula (3) with an alkoxysilane compound of formula (I-7) below:

Formula (I-7)

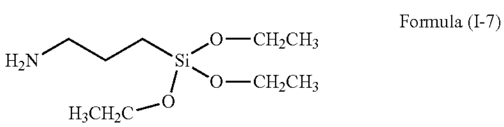

As for the compounds of formulae (9) to (16), they may be manufactured by a synthesis process which comprises the following steps:

a) synthesis of the compound of formula D below:

Formula D

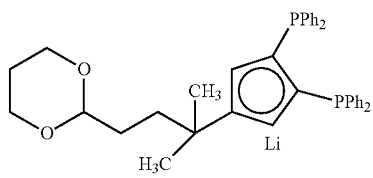

b) synthesis of a cyclopentadienyl salt of a metal M, preferably lithium or sodium, having the formula G below:

Formula G

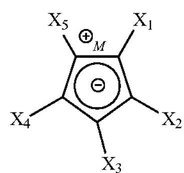

in which $X^1$, $X^2$, $X^3$, $X^4$, and $X^5$ are as defined above for the asymmetrical compounds of formula (I), c) reaction of the compound obtained in step b) with an iron salt and compound D.

More specifically, the compound of formula (9) is synthesized, according to the invention, by a process which comprises the reaction steps of the general process for synthesis of the compounds of formulae (9) to (16) described above, and using a compound of formula G in which $X^1$=$X^4$=H, $X^2$=$X^3$=$PPh_2$, $X^5$=t-Bu, and M=Li.

The compound of formula (10) may be manufactured according to the general process for synthesis of the compounds of formulae (9) to (16) described above, using a compound E in which $X^1$=$X^2$=$X^4$=$X^5$=H, $X^3$=P(i-Pr)$_2$ and M=Li.

The compound of formula (11) may be manufactured, according to the invention, by a process which comprises the reaction steps of the general synthesis process of the compounds of formulae (9) to (16), using a compound G in which M=Li, $X^1$=$X^2$=$X^4$=$X^5$=H, and $X^3$=P($R^4$)$_2$, in which $R^4$ is selected from a $C_3$ to $C_7$ aryl, or cyclic or acyclic aliphatic, group, or a saturated or unsaturated, linear or branched $C_1$ to $C_{30}$, preferably $C_3$ to $C_{10}$, more preferably $C_3$ to $C_5$ alkyl group which may contain at least one heteroatom, preferably N and/or O. Preferably $R^4$ is a cyclohexyl, tert-butyl, or phenyl, or furyl, group, which are optionally substituted, preferably by at least one methyl or methoxy group, a halogen atom such as F, Cl, Br, or I, preferably F or Cl, or by a $CF_3$ group.

The compound of formula (12) may be synthesized, according to the invention, by the process for general synthesis of the compounds of formulae (9) to (16) described above, using a compound G in which M=Li, $X^1$=$X^2$=$X^4$=H, $X^3$=P($R^4$)$_2$, $X^5$=t-Bu, in which $R^4$ is selected from a $C_3$ to $C_7$ aryl, or cyclic or acyclic aliphatic, group, or a saturated or unsaturated, linear or branched $C_1$ to $C_{30}$, preferably $C_3$ to $C_{10}$, more preferably $C_3$ to $C_5$ alkyl group, which may contain at least one heteroatom, preferably N and/or O. Preferably $R^4$ is an isopropyl, cyclohexyl, tert-butyl, or phenyl, or furyl, group, which are optionally substituted, preferably by at least one methyl or methoxy group, or a halogen atom such as F, Cl, Br, or I, preferably F or Cl, or a $CF_3$ group.

The compound of formula (13) may be synthesized, according to the invention, by a process which comprises the reaction steps of the process for synthesis of the compounds of formulae (9) to (16) described above, using a compound G in which M=Li, $X^1$=$X^2$=$X^4$=H, $X^3$=P($R^4$)$_2$, $X^5$=P($R^6$)$_2$, in which $R^4$ and $R^6$ are, independently of one another, selected from a $C_3$ to $C_7$ aryl, or cyclic or acyclic aliphatic, group, or a saturated or unsaturated, linear or branched $C_1$ to $C_{30}$, preferably $C_3$ to $C_{10}$, more preferably $C_3$ to $C_5$ alkyl group, which may contain at least one heteroatom, preferably N and/or O. Preferably $R^4$ and $R^6$ are, independently of one another, an isopropyl, cyclohexyl, tert-butyl, or phenyl, or furyl, group, which are optionally substituted, preferably by at least one methyl or methoxy group, or a halogen atom such as F, Cl, Br, or I, preferably F or Cl, or a $CF_3$ group.

The compound of formula (14) may be manufactured by a process according to the invention which comprises the reactions of the general synthesis process for compounds of formulae (9) to (16) described above, using a compound G in which $X^1$=$X^2$=$X^4$=$X^5$=H, $X^3$=C($CH_3$)$_2$—P($R^3$)$_2$, and M=Li; $R^3$ is selected from a $C_3$ to $C_7$ aryl, or cyclic or acyclic aliphatic, group, or a saturated or unsaturated, linear or branched $C_1$ to $C_{30}$, preferably $C_3$ to $C_{10}$, more preferably $C_3$ to $C_5$ alkyl group which may contain at least one heteroatom, preferably N and/or O. Preferably $R^3$ is an isopropyl, cyclohexyl, tert-butyl, or phenyl, or furyl, group, which are optionally substituted, preferably by at least one methyl or methoxy group, halogen (F, Cl, Br, or I), preferably F or Cl, or $CF_3$ group. More preferably $R^3$ is a substituted or unsubstituted phenyl group.

The compound of formula (15) may be manufactured, according to the invention, by the synthesis process described above for the compounds of formulae (9) to (16), using a compound G in which $X^1$=$X^2$=$X^4$=$X^5$=H, $X^3$=CHO, and M=Na.

The compound of formula (16) may be manufactured, according to the invention, by the reaction of the compound of formula (15) with a secondary amine in the presence of NaBH(OAc)$_3$, the secondary amine having the formula HN($R^5$)$_2$ in which $R^5$ is a $C_3$ to $C_7$ aryl, or cyclic or acyclic aliphatic, group, or a saturated or unsaturated, linear or branched $C_1$ to $C_{30}$, preferably $C_3$ to $C_{10}$, more preferably $C_3$ to $C_5$ alkyl group which may contain at least one heteroatom, preferably N and/or O. Preferably $R^5$ is an ethyl, isopropyl, cyclohexyl, tert-butyl, or phenyl, or furyl, group, which are optionally substituted, preferably by at least one methyl or methoxy group, or a halogen atom such as F, Cl, Br, or I, preferably, F or Cl, or a $CF_3$ group. $R^5$ is more preferably an ethyl group.

The compounds of formulae (17) and (18) may be manufactured by a synthesis process which comprises the following steps:

a) synthesis of the compound of formula F below:

Formula F

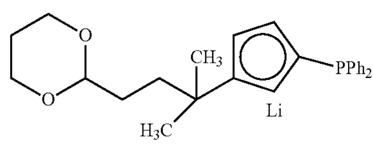

b) synthesis of a cyclopentadienyl salt of a metal M, preferably lithium or sodium, having the formula G below:

Formula G

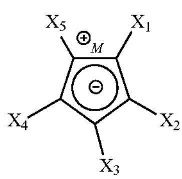

in which $X^1$, $X^2$, $X^3$, $X^4$, and $X^5$ are as defined above in the compounds of formulae (9) to (14), for the asymmetrical compounds of formulae (17) or (18), c) reaction of the compound obtained in step b) with an iron salt and the compound F.

In the course of the synthesis of the compounds according to the invention, the intermediate compounds A and B, C, D, and F were synthesized.

To the knowledge of the inventors, these compounds were hitherto unknown.

They are therefore also a subject of the invention.

Accordingly, the invention relates to:

a compound of formula A below:

Formula A

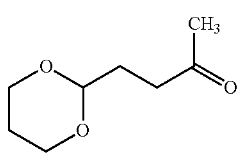

a compound of formula B below:

Formula B

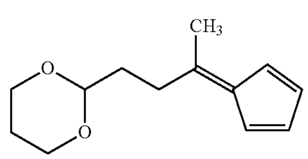

a compound of formula C below:

Formula C

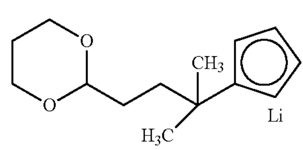

a compound of formula D below:

Formula D

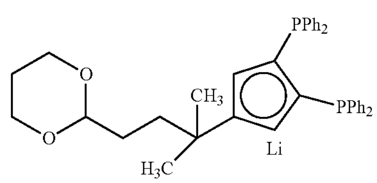

a compound of formula F below:

Formula F

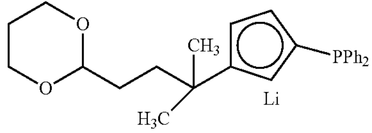

The supported ligand compounds of the invention, and more particularly the compounds (1) to (18), are subsequently:

either complexed with a catalytic metal, and then immobilized on a support by grafting of the reactive groups of the ligand compound in question with the reactive groups of the support, or first immobilized on the support and then complexed with the catalytic metal.

The complexation of the ligand compound according to the invention, or of the supported ligand compound according to the invention, takes place by dissolving or suspending in a conventional solvating medium (preferably $CH_2Cl_2$, $CHCl_3$, toluene, acetonitrile, dimethylformamide, dioxane, methanol, ethanol, water), with vigorous stirring, a precursor of the transition metal complexes (as mentioned above, for example palladium salt $PdCl_2$ or copper salt CuI), and carrying out reaction with the ligand compound or supported ligand compound in this medium, at ambient temperature (between 15 and 25° C.) if the medium is homogeneous, or at a temperature between 50 and 80° C. if the medium is heterogeneous, in order to facilitate complexing.

Accordingly, a ligand compound according to the invention is particularly adapted for the manufacture of a supported catalyst, by complexation with a catalytic metal.

The complexes or supported catalysts according to the invention, obtained in this way, have been found to be particularly suitable in processes for catalytic coupling of nucleophilic or electrophilic compounds, such as a carbon-carbon, or carbon-nitrogen, or carbon-oxygen coupling.

In order to make the invention better understood, a description will now be given, by way purely of illustration and not of limitation, of practical examples.

EXAMPLE 1

Synthesis of the Compound of Formula (1)

The compound of formula (1) is a ferrocenyl tetraphosphine ligand functionalized by a vinyl group.

In this compound, the spacer is a $—CH_2—$ chain element and the functional group is the vinyl group $—CH{=}CH_2$.

This compound was synthesized as follows:

a) Introduction of the C═C Double Bond

The first step is to introduce the desired double bond into the 6,6-dimethylfulvene of formula below:

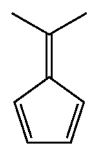

The reaction between this fulvene and allylmagnesium bromide has already been described by Vos and Jutzi in *Syn-*

*thesis* 2000, 3, 357, and allows the cyclopentadiene fragment to be obtained readily with a 60% yield after purification. This method has the advantage of using simple reactants: 6,6-dimethylfulvene is synthesized in large quantities in the laboratory, and allylmagnesium bromide is available commercially (2M in THF).

The diene was obtained after distillation (67° C. at 22 mm Hg) with a 60% yield. Its lithiation in hexane with n-BuLi (1.6 M in hexane) at −80° C. gave 1-[2-(2-methyl)pent-4-enyl]cyclopentadienyllithium in the form of a white powder with a 98% yield. This compound was characterized by $^{1}$H NMR by the appearance of a vinyl-type spin system: two doublets of doublets at 4.91 and 5.03 ppm, and a multiplet at 5.92 ppm.

b) Phosphinations of the 1-[2-(2-methyl)pent-4-enyl]-cyclopentadienyllithium

The 1-[2-(2-methyl)pent-4-enyl]cyclopentadienyl was subsequently employed in phosphination reactions. These reactions were conducted conventionally. The presence of the pseudo tert-butyl (gem-dimethyl) steers the disubstitution of the phosphines to 1,2 rather than 1,3, which is preferred when there is no prior substitution of the positions on the ring.

The first phosphination leads to 1-diphenylphosphino-3-[2-(2-methyl)pent-4-enyl]cyclopentadienyllithium in the form of an off-white solid, with a 90% yield, characterized in $^{31}$P NMR by a singlet at −21.1 ppm.

The second phosphination proceeds under the same conditions, and gives 1,2-bis(diphenylphosphino)-4-[2-(2-methyl)pent-4-enyl]cyclopentadienyllithium in the form of an off-white solid, with an overall yield of 80%, characterized in $^{31}$P NMR by a singlet at −22.5 ppm.

c) Synthesis of 1,1',2,2'-tetrakis(diphenyl-phosphino)-4,4'-bis[2-(2-methylpent-4-enyl)]ferrocene The compound obtained in step b) was subsequently put up against 0.5 equivalent of $FeCl_2$ to give, after 24 hours at reflux in toluene, and purification by chromatography on silica gel (toluene/hexane 1:1 then 2:1), a red solid with a 20% yield.

The $FeCl_2$ used is in the form of beads. To enhance the efficiency of the reaction, the beads had been crushed beforehand by magnetic stirring in the reaction solvent, a few hours before the addition of the organolithium compound, so as to give a fine powder.

The ferrocenyl derivative of formula (1) was characterized by $^{1}$H, $^{31}$P, and $^{13}$C NMR and by DRX. The $^{1}$H and $^{13}$C NMR spectra are in agreement with the expected structure. The $^{31}$P NMR spectrum shows two multiplets centered on −30.6 ppm and 34.5 ppm, which are typical of the expected AA'BB' spin system.

The production of this spectrum indicates that the conformation of the ligand has indeed been preserved. Crystals analyzable by DRX were obtained by diffusing a toluene solution of the ligand in hexane. The resulting structure confirms that the cyclopentadienyl rings are positioned in a conformation identical to that found for the corresponding unfunctionalized ligand.

EXAMPLE 2

Synthesis of the Compounds of Formula (2) and (3)

The compound of formula (2) is a ferrocenyl tetraphosphine ligand functionalized by a ketonic functional group. Two pathways which utilize the organometallic compounds were used to synthesize this ligand.

This first pathway used an organozinc compound, and the second pathway used an organomagnesium compound. In the first pathway, the first step is to form an organozinc compound, and then to subject it to Negishi coupling with acetyl chloride.

The synthesis of an organozinc compound by direct insertion of zinc with bromides and iodides, through the addition of lithium chloride, was described by Knochel et al. in *Angew. Chem. Int. Ed.* 2006, 45, 6040.

This method was applied according to the following general scheme:

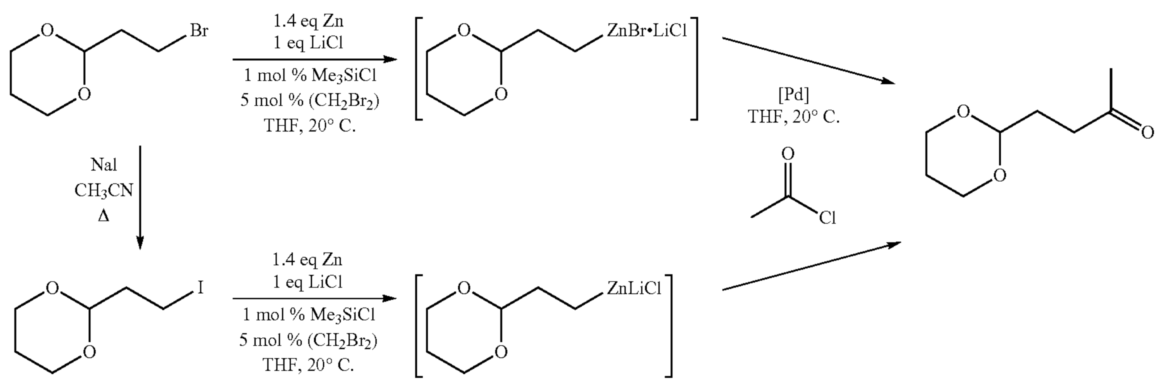

This gives 4-(1,3-dioxan-2-yl)butan-2-one of formula A below:

Formula A

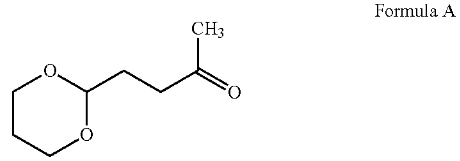

In the second pathway, the first step is to form an organomagnesium compound from 2-(2-bromoethyl)-1,3-dioxolane, and then to subject it to addition with acetyl chloride, according to the following scheme:

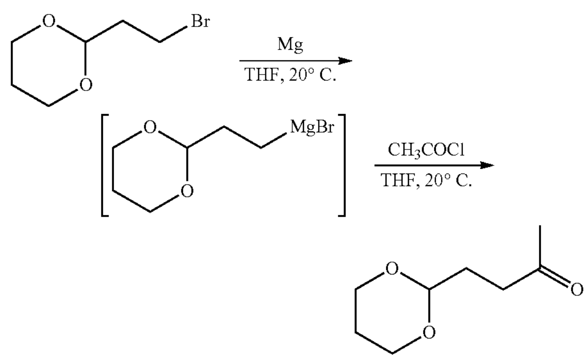

This gives 4-(1,3-dioxan-2-yl)butan-2-one of formula A below:

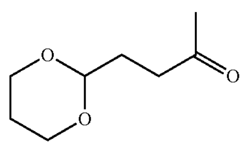

This ketone of formula A was subsequently employed in the formation of 2-[3-(cyclopenta-2,4-dienylidene)butyl]-1,3-dioxane, by the action of pyrrolidine and lithiated cyclopentadiene.

The maximum yield was achieved by using 1.1 equivalents of pyrrolidine, which was added approximately 2 minutes before the addition of the solution of 1.5 equivalents of lithiated cyclopentadiene in THF.

The mixture is then obtained with stirring for approximately one hour at ambient temperature.

2-[3-(Cyclopenta-2,4-dienylidene)butyl]-1,3-dioxane of formula B below:

Formula B

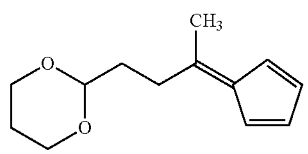

was characterized in $^{1}$H NMR by the appearance of an unresolved peak at around 6.5 ppm, corresponding to the cyclopentadiene.

$^{13}$C NMR, the signal corresponding to the carbon of the carbonyl group (208.3 ppm) is shifted to 143.2 ppm, and in IR spectroscopy a band which is characteristic of alkenes, at 1639 $cm^{-1}$, appears.

The fulvene obtained is immediately reacted in the next step for the introduction of a methyl group onto the carbon 6 of the fulvene, to give the pseudo tert-butyl.

This was carried out by the action of methyllithium on the compound of formula B in diethyl ether at −° C.

This gives the 1-[4-(1,3-dioxan-2-yl)-2-methylbutyl]cyclopentadienyllithium of formula C below, in a quantitative yield:

Formula C

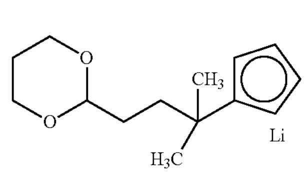

The progress of the reaction can easily be observed: the solution of fulvene is bright yellow and, as the reaction progresses, a white precipitate appears and the solution loses its color, eventually becoming colorless.

Filtering and washing under argon of the resulting precipitate give the compound C in the form of a white powder.

This cyclopentadienyllithium derivative was characterized in $^{1}$H NMR by the shielding of the unresolved peak formed by the protons of the cyclopentadiene, from 6.5 ppm to 5.6 ppm.

The cyclopentadienyllithium derivative of formula C then underwent two successive phosphination steps by addition, successively, of stoichiometric amounts of $ClPPh_2$ and then n-BuLi.

The compound of formula D below is then obtained, with an overall yield of 80% to 90% over the two phosphination steps:

Formula D

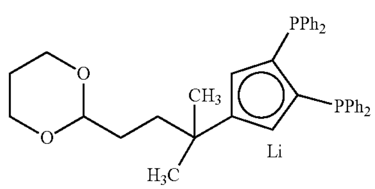

This compound was characterized in $^{1}$H NMR by the disappearance of two protons of the cyclopentadienyl ring and by the appearance of an unresolved peak between 7.0 and 7.5 ppm. The $^{31}$P NMR shows the appearance of a singlet at −25.2 ppm.

Subsequently, two equivalents of diphosphinyl organolithium compound of formula D were reacted with one equivalent of $FeCl_2$ in toluene or THF, with heating at reflux.

This compound obtained was purified by chromatography on silica gel.

This gives the compound of formula (2) below, in the form of a red powder with a 50% yield: 1,1',2,2'-tetrakis(diphenylphosphino)-4,4'-di[4-(1,3-dioxan-2-yl)-2-methylbut-2-yl]ferrocene.

Formula (2)

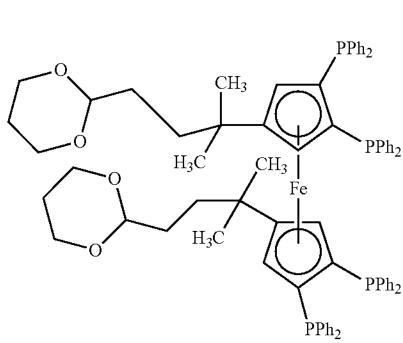

This compound of formula (2) can also be synthesized by a “one-pot” method starting from the compound of formula C, which is a lithiated compound which is, however, not a phosphinyl compound; by reacting the compound of formula C, by adding, in a first step, a stoichiometric amount of $PPh_2Cl$ and n-BuLi at −80° C., and then again adding a stoichiometric amount of $PPh_2Cl$ and n-BuLi at −80° C., followed, still in the same reaction mixture, by the addition of 0.5 equivalent of $FeCl_2$ per one equivalent of compound of formula C, in toluene with heating at reflux.

The resulting product is purified by chromatography on silica gel. The reaction yield is also 50%.

The compound of formula (2) was characterized by 1H $^{31}P$, and $^{13}C$ NMR, exact mass, and X-ray diffraction.

The exact mass analysis and the proton and carbon NMR spectra confirm the formation of the target ferrocenyl derivative.

The $^{31}P$ NMR spectrum again shows coupling patterns which are identical to the model compound: an AA'BB' spin system, including two multiplets centered on −30.35 and −34.4 ppm, which guarantee the right conformation of the phosphorus atoms and their mutual spatial proximity.

The structure obtained by X-ray diffraction effectively shows the eclipsed conformation of the cyclopentadiene rings of the ferrocene. It can also be seen that in the solid state, the ketal groups are oriented in opposite directions.

The compound of formula (3) is synthesized by liberating the functional group of the compound of formula (2), so as to have a heterogeneizable ligand.

The deprotection of ferrocenyl aldehydes is not described specifically in the literature as far as the inventors are aware. Tests were therefore conducted of a method for conventional deprotection for the 1,3-dioxane compounds, as described in “*Protective groups in Organic Synthesis, Third Edition*” by T. W. Greene and P. G. M. Wuts (1999 John Wiley & Sons).

However, these methods did not produce deprotection of the aldehyde, since they never resulted in complete deprotection (75% at best).

But the inventors discovered, surprisingly, that the use of microwaves allowed the aldehydes to be deprotected quantitatively.

The apparatus used permits a pressure greater than atmospheric pressure to be established, and hence allows the mixture to be heated above its boiling point under standard conditions.

Accordingly, using microwave radiation with a power of 100 W on 300 mg of compound and 15 ml of solvent at 120° C., at around 4 bar pressure in THF (THF/HCl 3N for 20 minutes), deprotection proves to be total, and the dialdehyde is obtained with a yield of more than 90% after purification by chromatography on silica gel. This then gives the compound of formula (3): 1,1',2,2'-tetrakis(diphenylphosphino)-4,4'-di(4-oxo-2-methylbut-2-yl)ferrocene.

This compound is characterized in $^{1}H$ NMR by the disappearance of the signals due to the protective groups (proton of the ketal at 4.47 ppm) and by the appearance of the signal corresponding to the aldehydic proton at 9.77 ppm. Similarly, in $^{13}C$ NMR, the signals of the ketal no longer appear, and a signal at 202.0 ppm, which is typical of carbonyls, has appeared. In IR spectroscopy, a band at 1721.8 $cm^{-1}$ is observed.

The $^{31}P$ NMR spectrum still possesses the same appearance of an AA'BB' spin system, but the chemical shifts of two multiplets have slightly changed: they are shielded by approximately 0.4-0.5 ppm to −30.9 and −34.9 ppm.

EXAMPLE 3

Immobilization of the Compound of Formula (3)

This immobilization was carried out by grafting onto a polystyrene-methylamine resin, identified as PL-AMS.

For this, a condensation reaction between the polystyrene-methylamine resin and the heterogeneizable ligand compound of formula (3) was carried out by reductive amination in 1,2-dichloroethane in the presence of sodium triacetoxyborohydride.

This reducing agent is specific to imines, and has the advantage of not giving rise to potentially toxic byproducts, as $NaBH_3CN$ may do. The resin was suspended 30 minutes before the addition of the reactants, to cause it to swell and to allow access to the reaction sites within the beads. After 24 hours of reaction, the reaction mixture was neutralized with 1M aqueous NaOH solution, and then the resin was washed thoroughly with $CH_2Cl_2$ in order to remove the unreacted product.

The resin obtained is purely heterogeneous, and is not soluble in any solvent. Moreover, to verify the integrity of the ligand, a $^{31}P$ CP-MAS NMR analysis was carried out.

The spectrum was obtained at a rotary speed of 14 kHz, and reveals the presence of a signal centered on −30 ppm. This shift is in agreement with the shift observed for the corresponding ligand in solution, and shows that the phosphines have not been altered during their grafting onto the resin; more particularly, the phosphorus atoms are not oxidized, as shown by this chemical shift in NMR.

EXAMPLE 4

Synthesis of the Compound of Formula (4)

To obtain the compound of formula (4), the compound of formula (3) was subjected to reduction.

The carbonyl reduction was carried out by $LiAlH_4$ at 0° C. in THF.

Reaction is complete after 1 hour and requires no purification after the conventional treatment of the reaction mixture; it gives, quantitatively, the compound of formula (4), i.e., 1,1',2,2'-tetra-kis(diphenylphosphino)-4,4'-di(4-hydroxy-2-methylbut-2-yl)ferrocene, characterized by the disappearance in $^{1}H$ NMR of the signal at 9.77 ppm, and the appearance of a signal corresponding to the protons of the methylene group $\alpha$ to the oxygen (3.62 ppm). Similarly, in $^{13}C$ NMR, the carbonyl carbon signal at 202.0 ppm is shifted upfield to 63.6 ppm. The $^{31}P$ NMR spectrum remains unchanged.

EXAMPLE 5

Synthesis of the Compound of Formula 5

Method A:

A solution of triphenyl(4-vinylbenzyl)phosphonium iodide (0.68 g, 1.33 mmol, 3 eq) in 15 ml of THF is admixed at ambient temperature (AT) with NaH (32 mg, 1.35 mmol, 3 eq). Compound (3) (0.5 g, 0.45 mmol, 1 eq) in solution in 5 ml of THF is added dropwise to the phosphonium solution. After 30 minutes at AT, the reaction mixture is neutralized with saturated aqueous $NH_4Cl$ solution, then extracted with twice 20 ml of $CH_2Cl_2$. After washing with saturated aqueous NaCl solution, the organic phase is dried over $MgSO_4$ and then concentrated under reduced pressure to give, after purification by chromatography on silica gel (AcOEt/hexane 1:4), 300 mg (ρ=50%) of 1,1',2,2'-tetrakis(diphenylphosphino)-4,4'-bis[2-methyl-6-(4-vinylphenyl)hex-5-en-2-yl]ferrocene in the form of a red powder.

Method B:

A solution of compound (3) (0.1 g, 89 μmol, 1 eq) in 1.5 ml of THF is admixed with 2-(4-vinyl-benzylsulfonyl)benzo[d]thiazole (0.06 g, 0.19 mmol, 2.1 mmol) and then NaHMDS (0.1 ml, 2 M in THF, 2.1 eq) at AT. After 30 minutes at AT the reaction mixture is neutralized with saturated aqueous $NH_4Cl$ solution and extracted with 2×20 ml of $CH_2Cl_2$. After washing with saturated aqueous NaCl solution, the organic phase is dried over $MgSO_4$ and then concentrated under reduced pressure to give, after purification by chromatography on silica gel (AcOEt/hexane 1:4), 41 mg (ρ=35%) of 1,1',2,2'-tetrakis(diphenylphosphino)-4,4'-bis[2-meth-yl-6-(4-vinylphenyl)hex-5-en-2-yl]ferrocene in the form of a red powder. The $^{31}P$ NMR spectrum preserves, as expected, the AA'BB' spin system appearance, with slightly modified chemical shifts. $^1H$ NMR ($CDCl_3$, 600 MHz, 298 K): δ (ppm) 6.41-8.44 (m, 50H), 6.42 (d, 2H, $^3J$=16.8 Hz), 6.22 (m, 2H), 5.77 (d, 2H, $^3J$=17.4 Hz), 5.25 (d, 2H, $^3J$=11.4 Hz), 4.10, 4.23 (s, 2H), 1.94, 2.12 (m, each 2H), 1.28, 1.38 (m, each 2H), 0.18, 1.07 (s, each 6H). $^{31}P$ NMR ($CDCl_3$, 121.48 MHz, 298 K): δ (ppm) −30.8 (m, 2P), −34.9 (m, 2P). $^{13}C$ NMR ($CDCl_3$, 150.9 MHz, 298 K): δ (ppm) 126.1-139.0 (m, 60C), 136.5 (s, 2C), 131.2 (s, 2C), 129.4 (s, 2C), 113.4 (s, 2C), 105.5 (s, 2C), 88.1 (m, 2C), 79.7 (m, 2C), 72.6, 72.1 (s, each 2C), 46.7 (s, 2C), 33.3 (s, 2C), 28.8 (s, 2C), 28.6, 27.1 (s, each 2C). IR ν ($cm^{-1}$): 1476.2, 1433.2.

$C_{88}H_{83}P_4Fe$ (MW 1319.33, exact mass 1318.47): m/z 1319.483 (M+); simulated 1319.479 (σ=0.083).

EXAMPLE 6

Synthesis of the Compound of Formula (6)

The compound of formula (6) was obtained by reductive amination of compound (3) with the amine of formula below:

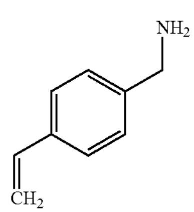

by a Staudinger reaction in accordance with the method described by Ahuji et al., *J. Polym. Sci. Pol. Chem.* 2005, 43, 3411.

The reductive amination is carried out in dichloroethane in the presence of three equivalents of sodium triacetoxyborohydride, and leads, after purification by chromatography, to the compound of formula (6) with a 55% yield.

The compound of formula (6), namely 1,1',2,2'-tetrakis(diphenylphosphino)-4,4'-[2-methyl-5-(4-vinylbenzylamino)pent-2-yl]ferrocene, was characterized by exact mass spectrometry with the detection of an unresolved peak centered on m/z=1353.353. In $^1H$ NMR, the disappearance of the signal at 9.77 ppm and the appearance of signals typical of a vinyl-type spin system between 5 and 6 ppm are observed.

Similarly, in the $^{13}C$ NMR spectrum, the signal corresponding to the carbonyl at 202.0 ppm disappears, and $sp^2$ carbon signals at 136.8 and 113.8 ppm and also the signal of the benzylic carbon at 53.4 ppm are seen to appear. The $^{31}P$ NMR spectrum still has the same AA'BB' spin system appearance.

EXAMPLE 7

Immobilization of the Compound of Formula (6) by polymerization

The compound of formula (6) was immobilized by copolymerization with a monomer of formula below:

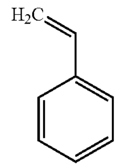

In a 100 ml round-bottom flask, 1.54 g of styrene (14.8 mmol) and 0.260 g of ferrocenyl phosphine (0.2 mmol) are introduced in 50 ml of toluene. The mixture is degassed by the sparging of nitrogen for 1 hour, and then 0.04 g of azobisisobutyronitrile (AIBN) is added as a radical polymerization initiator.

The reaction mixture is then held at 85° C. with magnetic stirring for 48 hours. After this time, the toluene is evaporated, and a minimum amount of THF is added in order to dissolve the polymeric residue.

The THF solution is added dropwise to 50 ml of methanol cooled to 0° C. by an ice bath. The insoluble polymer slowly precipitates from the methanol.

At the end of the addition, the polymer in suspension in methanol is filtered on a glass frit, rinsed with a minimum amount of methanol, and dried under vacuum to give a final mass of 1.14 g.

The expected compound corresponds to the following formula:

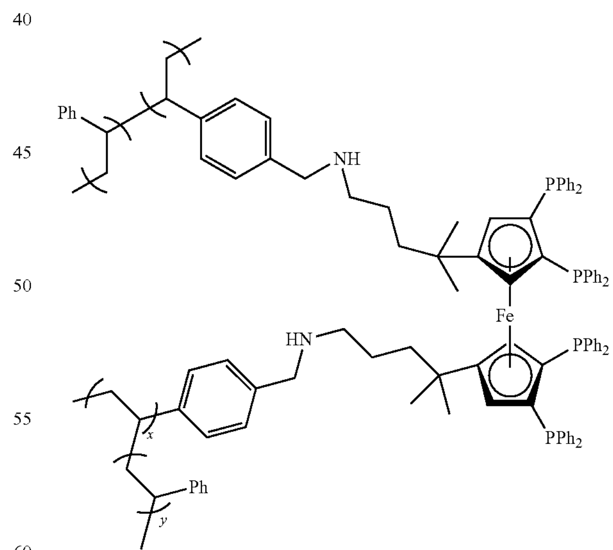

Phosphorus NMR in solution confirms that this supported ligand compound is obtained, with the conformational control of the ligand of formula (6) as demonstrated by the two multiplets centered at −34.30 and −30.30 ppm in phosphorus NMR in solution in deuterated chloroform (AA'BB' spin system).

The resulting polymer has a strong red coloring and is soluble in solvents such as THF, $CHCl_3$, $CH_2Cl_2$, toluene, $Et_2O$, and ethyl acetate, but is insoluble in hexane and methanol. Elemental analysis of this polymer showed a phosphorus content of 1.05%, corresponding to a ligand loading of 0.085 mmol/g.

The catalytic performance of the supported ligands according to the invention was proven in catalysis of carbon-carbon coupling.

Example 8 below shows this catalytic performance.

EXAMPLE 8

Acylation Coupling Reaction of Phenylboronic Acid with the Deactivated Compound 4-Methoxy-Bromobenzene by the Compound of Formula (6) Supported on Polystyrene Resin, and Recovery of the Catalyst This carbon-carbon coupling reaction was carried out under the following conditions of low metallic loads (<1%, reaction conditions not optimized): a solid mixture of phenylboronic acid (0.26 g, 2.13 mmol), potassium carbonate (0.30 g, 2.17 mmol), the polymeric supported ligand compound obtained from compound (6) (0.125 g of polymer resin containing 0.085 mmol/g of tetraphosphine ligand, or 0.01065 mmol), and the palladium precursor $[Pd(C_3H_5)Cl]_2$ (1.9 mg, 0.0052 mmol) is placed under argon in a Schlenk tube. 1 ml of DMF, distilled and degassed by sparging with nitrogen, is added, and the mixture is held at 80° C. with vigorous stirring for five minutes. 4-Bromoanisole (0.41 g, 265 μl, 2.17 mmol), distilled and degassed, is added by syringe to the reaction mixture, which is held at 120° C. for 20 hours. The cooled mixture is evaporated to dryness under vacuum, and the residue is dissolved in 10 ml of ethyl ether and extracted with 10 ml of water. The organic phases are dried over magnesium sulfate and, after evaporation of the ether under vacuum, the residue is dissolved in 30 ml of methanol for separation of the palladium-complexed resin (catalyst). The resulting precipitate (catalyst) is filtered off, and the coupling product is obtained with a 50% yield after evaporation of the solvent and chromatographic treatment.

It should be noted that the great majority of couplings of this type using resins, in the literature, are carried out using iodides and in the presence of metallic loads which exceed 1 mol % (N. T. S. Phan et al. *Adv. Synth. Catal.* 2006, 348, 609-679, see pp. 636-650 and references cited). Here, 4-methoxybromobenzene is known to be a substrate which is difficult to couple owing to its electron-rich nature (see J.-C. Hierso et al. *Eur. J. Inorg. Chem.* 2007, 3760-3780). In the absence of a ligand, Buchwald and coauthors reported the deficiency of coupling in the presence of palladium acetate, whereas 4-bromoacetophenone (activated substrate, electron-deficient) is effectively coupled to phenylboronic acid (see Buchwald et al. *Ang. Chem. Int. Ed.* 1999, 38, 2413-2416, and J. Am. Chem. Soc. 1999, 121, 9550-9561).

EXAMPLE 9

Arylation Coupling Reaction of Phenylboronic Acid with Bromobenzene by the Compound of Formula (6) Supported on Polystyrene Resin, and Recovery of the Catalyst This carbon-carbon coupling reaction was carried out under the following conditions of low metallic loads <0.5 mol %: a solid mixture of phenylboronic acid (0.26 g, 2.13 mmol), potassium carbonate (0.30 g, 2.17 mmol), the polymeric supported ligand compound obtained from compound (6) (0.125 g of polymer resin containing 0.085 mmol/g of tetraphosphine ligand, or 0.01065 mmol), and the palladium precursor $[Pd(C_3H_5)Cl]_2$ (1.9 mg, 0.0052 mmol) is placed under argon in a Schlenk tube. 1 ml of DMF, distilled and degassed by sparging with nitrogen, is added, and the mixture is held at 80° C. with vigorous stirring for five minutes. Bromobenzene (0.34 g, 230 μl, 2.17 mmol), distilled and degassed, is added by syringe to the reaction mixture, which is held at 120° C. for 20 hours. The cooled mixture is evaporated to dryness under vacuum, and the residue is dissolved in 10 ml of ethyl ether and extracted with 10 ml of water. The organic phases are dried over magnesium sulfate and, after evaporation of the ether under vacuum, the residue is dissolved in 20 ml of methanol for separation of the palladium-complexed resin (catalyst). The resulting precipitate (catalyst) is filtered off, and GC analysis of the solution indicates total conversion of the bromobenzene into coupling product, which is obtained with an 80% yield and isolated after separation of the heterogeneous catalyst, followed by evaporation of the organic solvent containing the product, and chromatographic treatment. The catalyst isolated by filtration is reused in reaction according to the same procedure. GC analysis again shows total conversion of the bromobenzene into coupling product, which is obtained with an 80% yield after evaporation of the solvent and chromatographic treatment. The isolated catalyst can be reused in this way a number of times (six times) with no significant drop in activity, the limitation lying in the losses during filtration.

EXAMPLE 10

Arylation Coupling Reaction of Phenylboronic Acid with Bromoacetophenone by the Compound of Formula (6) Supported on Polystyrene Resin, and Recovery of the Catalyst This carbon-carbon coupling reaction was carried out under the following conditions of low metallic loads <0.5 mol %: a solid mixture of phenylboronic acid (0.26 g, 2.13 mmol), potassium carbonate (0.30 g, 2.17 mmol), bromoacetophenone (0.43 g, 2.17 mmol), the polymeric supported ligand compound obtained from compound (6) (0.125 g of polymer resin containing 0.085 mmol/g of tetraphosphine ligand, or 0.01065 mmol), and the palladium precursor $[Pd(C_3H_5)Cl]_2$ (1.9 mg, 0.0052 mmol) is placed under argon in a Schlenk tube. 1 ml of DMF, distilled and degassed by sparging with nitrogen, is added, and the mixture is held at 120° C. for 20 hours. The cooled mixture is evaporated to dryness under vacuum, and the residue is dissolved in 10 ml of ethyl ether and extracted with 10 ml of water. The organic phases are dried over magnesium sulfate and, after evaporation of the ether under vacuum, the residue is dissolved in 20 ml of methanol for separation of the palladium-complexed resin (catalyst). The resulting precipitate (catalyst) is filtered off, and GC analysis of the solution indicates total conversion of the bromoacetophenone into coupling product, which is isolated with a 65% yield after evaporation of the solvent and chromatographic treatment. The catalyst isolated by filtration is reused in reaction according to the same procedure. GC analysis again shows total conversion of the bromoacetophenone into coupling product, which is obtained with a 65% yield after evaporation of the solvent and chromatographic treatment. The isolated catalyst can be reused in this way a number of times (six times) with no significant drop in activity, the limitation lying in the losses during filtration.

EXAMPLE 11

Synthesis of the Compound of Formula 7

The compound of formula (4) (50 mg, 44 μmol) is dissolved in 1 ml of dichloromethane. (3-Isocyanatopropyl)triethoxysilane (24 μl, 90 μmol) is introduced into the reaction mixture and then one drop of triethylamine is added. After 20 hours at ambient temperature, the mixture is concentrated under vacuum to give 70 mg, in a 95% yield, of product in the form of a red powder. The $^{31}$P NMR spectrum preserves, as expected, the AA'BB' spin system appearance, with slightly modified chemical shifts. $^{1}$H NMR ($CDCl_3$, 500 MHz, 298 K): δ (ppm) 6.45-8.42 (m, 40H), 4.7 (broad s, 2H), 4.17-4.04 (s, each 2H), 4.02 (t, 4H, $^3J$=6.5 Hz), 3.82 (q, 12H, $^3J$=7 Hz), 3.20 (q, 4H $^3J$=6.5 Hz), 1.65 (m, 4H), 1.30 (m, 4H), 1.24 (t, 18H, $^3J$=7 Hz), 0.99, 0.13 (s, each 6H), 0.87 (m, 4H), 0.63 (s, 4H). $^{31}$P NMR ($CDCl_3$, 202.5 MHz, 298 K): δ (ppm)-30.7 (m, 2P), −34.6 (m, 2P). $^{13}$C NMR ($CDCl_3$, 125.7 MHz, 298 K): δ (ppm) 157.1 (s, 2C), 127.5-139.1 (m, 48C), 105.8 (s, 2C), 88.5 (dd, 2C, $^1J_{CP}$=35.2 Hz, $^2J_{CP}$=13.8 Hz), 79.9 (t, 2C, $J_{CP}$=18.9 Hz), 72.7, 72.2 (s, each 2C), 65.6 (s, 2C), 58.8 (s, 6C), 43.79 (s, 2C), 43.3 (s, 2C), 35.7 (s, 2C), 28.9, 27.2 (s, each 2C), 25.1 (s, 2C), 23.7 (s, 2C), 18.6 (s, 2C), 8.0 (s, 2C). $C_{90}H_{112}P_4FeO_{10}N_2Si_2$ (MW 1617.77, exact mass 1616.61): m/z 1616.613 $M^+$; simulated 1616.615 (σ=0.189).

EXAMPLE 12

Immobilization of the Compound of Formula 7 on Inorganic Support $SiO_2$ 1 g of silica (ACROS, Kieselgel 0.035-0.070 mm, 60 Å) is suspended in toluene in a Dean-Stark apparatus and is heated at reflux for 20 hours. The disilane compound (7) (300 mg, 185 μmol) in solution in 15 ml of toluene is added to the silica, and the reaction mixture is placed under reflux for 5 hours. After cooling, the mixture is concentrated under vacuum and the residue is then taken up in 20 ml of dichloromethane, isolated by filtration, washed thoroughly with dichloromethane, and then dried under vacuum to give 1.06 g of a red powder. The resulting solid is insoluble in all of the usual organic solvents tested (THF, $CHCl_3$, $CH_2Cl_2$, toluene, $Et_2O$, ethyl acetate, hexane, methanol, DMF, DMSO, NMP, etc.). $^{31}$P CP-MAS NMR analysis, obtained at a rotary speed of 14 Hz, reveals the presence of a signal centered on −30 ppm. This shift is in agreement with the shift observed for the corresponding ligand in solution.

EXAMPLE 13

Arylation Coupling Reaction of Phenylboronic Acid with Bromoacetophenone by the Compound of Formula (7) Supported on Inorganic Support $SiO_2$, and Recovery of the Catalyst This carbon-carbon coupling reaction was carried out under the following conditions of low metallic loads <0.5 mol %: a solid mixture of phenylboronic acid (0.26 g, 2.13 mmol), potassium carbonate (0.30 g, 2.17 mmol), bromoacetophenone (0.43 g, 2.17 mmol), the silica-supported ligand compound obtained from compound (7) (0.15 g of polymer resin containing 0.068 mmol/g of tetraphosphine ligand, or 0.0102 mmol), and the palladium precursor $[Pd(C_3H_5)Cl]_2$ (1.8 mg, 0.00549 mmol) is placed under argon in a Schlenk tube. 1 ml of DMF, distilled and degassed by sparging with nitrogen, is added, and the mixture is held at 120° C. for 20 hours. The cooled mixture is filtered to recover the ligand compound and the metal (less than 1 ppb of Pd, by ICP analysis, remaining in solution). The filtrate is evaporated to dryness under vacuum, and the residue is dissolved in 10 ml of ethyl ether with 10 ml of water for extraction. The organic phases are dried over magnesium sulfate. GC analysis beforehand indicates total conversion of the bromoacetophenone into coupling product, for an 85% yield after evaporation of the solvent and chromatographic treatment. The catalyst isolated by filtration is reused in reaction according to the same procedure. GC analysis again shows total conversion of the bromoacetophenone into coupling product, which is obtained with an 85% yield after evaporation of the solvent and chromatographic treatment. The isolated catalyst can be reused in this way a number of times (six times) with no significant drop in activity, the limitation lying in the losses during filtration.

EXAMPLE 14

Synthesis of the Compound of Formula 8

A solution of the compound of formula (3) (0.5 g, 0.41 mmol) in 20 ml of dichloromethane is admixed at ambient temperature with 3-amino(triethoxypropyl)silane (0.19 ml, 0.82 mmol) and one drop of acetic acid. The solution is taken to reflux for 5 hours and then concentrated under vacuum. The crude product is purified by chromatography on silica gel ($CH_2Cl_2$ eluent) to give the compound of formula (8) in the form of an orange powder (75% yield). The $^{31}$P NMR spectrum preserves, as expected, the AA'BB' spin system appearance, with slightly modified chemical shifts.

$^{1}$H NMR ($CDCl_3$, 500 MHz, 298 K): δ (ppm) 6.45-8.42 (m, 40H), 7.50 (t, 2H, $^3J$=5 Hz), 4.17-4.04 (s, each 2H), 3.82 (q, 12H, $^3J$=7 Hz), 1.63 (t, 4H, $^3J$=6.5 Hz), 1.56 (q, 4H, $^3J$=6.5 Hz), 1.35 (m, 4H), 1.30 (m, 4H), 1.24 (t, 18H, $^3J$=7 Hz), 0.99, 0.13 (s, each 6H), 0.63 (s, 4H). $^{31}$P NMR ($CDCl_3$, 202.5 MHz, 298 K): δ (ppm) −30.8 (m, 2P), −34.3 (m, 2P). The immobilization of the compound of formula (8) on inorganic $SiO_2$ support is carried out in the same way as for the compound (7).

EXAMPLE 15

Synthesis of the Compound of Formula 9 with $E=(CH_2)_3$ and GF=4-Vinylbenzylamine A suspension of $FeCl_2$ (1.1 g, 8.6 mmol) in toluene (20 ml) is admixed dropwise at −40° C. with a solution of 1,2-bis(diphenylphosphino)-4-tert-butylcyclopenta-dienyllithium (4.45 g, 8.9 mmol) in 30 ml of toluene. The solution is held with stirring for two hours following return to ambient temperature. A solution of 1,2-bis(diphenylphosphino)-3-[4-(1,3-dioxan-2-yl)-2-methylbutyl]cyclopentadienyllithium (5.07 g, 8.55 mmol) in 30 ml of toluene is subsequently added dropwise at −40° C. The mixture is taken to reflux for 15 hours. Following return to ambient temperature, the solution is washed with 50 ml of water and then with 50 ml of 0.5 M aqueous HCl solution. The aqueous phase is extracted with 50 ml of toluene, and the organic phases are then combined, dried over $MgSO_4$ and concentrated under reduced pressure. The crude product obtained is purified by chromatography on silica gel (AcOEt/heptane, 1:5) to give 1 g (ρ=11%) of 1,1',2,2'-tetrakis(diphenylphosphino)-4,4'-di-tert-butylferrocene, 3 g (ρ=32%) of 1,1',2,2'-tetrakis(diphenylphosphino)-4-[4-

(1,3-dioxan-2-yl)-2-methylbut-2-yl]-4'-tert-butylferrocene, and 2 g (ρ=22%) of desired 1,1',2,2'-tetrakis(diphenylphosphino)-4,4'-di[4-(1,3-dioxan-2-yl)-2-methylbut-2-yl]ferrocene. In contrast to the compounds of formula (1) to (8), the $^{31}$P NMR spectrum of the three products possesses an ABCD-type spectrum, owing to the asymmetry of the molecule, with different chemical shifts for the four phosphorus atoms. These shifts, however, cannot be extracted directly from the spectrum, but must be calculated by simulation (G-NMR). $^{1}$H NMR ($CDCl_3$, 300 MHz, 303 K): δ (ppm) 6.30-8.42 (m, 40H), 4.34 (m, 1H), 3.88-4.05 (m, 6H), 3.69 (m, 2H), 2.01 (m, 1H), 1.21-1.51 (m, 5H), 0.84 (s, 3H), 0.6 (s, 9H), 0.05 (s, 3H). $^{31}$P NMR ($CDCl_3$, 121.49 MHz, 303 K): δ (ppm) −30.0 (m, 2P), −33.9 (m, 2P). Calculated values: −29.9, −30.3, −33.9, −34.0 ppm. $^{13}$C NMR ($CDCl_3$, 75.46 MHz, 303 K): S (ppm) 127.4-139.4 (m, 48C), 107.7 (s, 1C), 105.7 (s, 2C), 103.1 (s, 2C), 88.3 (m, 2C), 79.7 (m, 2C), 73, 72.5 (m, each 2C), 72.0, 71.2 (d, each 2C, $J_{CP}$=5.3 Hz), 67.3, 61.2 (s, each 1C), 41 (s, 1C), 33.2 (s, 1C), 31.9 (s, 3C), 31.1, 30.7 (s, each 1C), 28.9, 27.3 (s, each 1C), 26.3 (s, 2C).

$C_{71}H_{71}P_4FeO_2$ (MW 1135.05, exact mass 1135.36): m/z 1135.3767 $M^+$; simulated 1135.3751 (σ=0.035).

For the deprotection leading to the actual compound of formula (9), with E=$(CH_2)_3$ and GF=4-vinyl-benzylamine, a solution of 1,1',2,2'-tetrakis(diphenyl-phosphino)-4-[4-(1,3-dioxan-2-yl)-2-methylbut-2-yl]-4'-tert-butylferrocene (0.1 g, 88 μmol) in 20 ml of THF is admixed with 5 ml of 2N hydrochloric acid solution. The solution is placed under microwave radiation (125 W) according to the following program: temperature rise 10° C./min to 120° C., then plateau at 120° C. for 10 min. After cooling, the reaction mixture is concentrated under vacuum, diluted with 20 ml of water, and extracted with 2 times 25 ml of $CH_2Cl_2$. The organic phase is dried over $MgSO_4$ and concentrated under reduced pressure. The crude product obtained is purified by chromatography on silica gel (eluent AcOEt/heptane 1:4) to give 90 mg (ρ=90%) of 1,1',2,2'-tetrakis(diphenylphosphino)-4-(4-oxo-2-methylbut-2-yl)-4'-tert-butylferrocene in the form of a red powder, for which the $^{31}$P NMR spectrum preserves, as expected, the ABCD spin system appearance, with slightly modified chemical shifts.

In a last step, a solution of $NaBH(OAc)_3$ (0.39 g, 1.8 mmol) and 4-vinylbenzylamine (0.3 g, 2.3 mmol) in 5 ml of dichloroethane is added dropwise at ambient temperature to a solution of 1,1',2,2'-tetrakis-(diphenylphosphino)-4-(4-oxo-2-methylbut-2-yl)-4'-tert-butylferrocene (1.3 g, 1.2 mmol) in 15 ml of dichloroethane. The solution is held with stirring for 24 hours and then neutralized by addition of 1 M aqueous sodium hydroxide solution. The aqueous phase is extracted with 2 times 30 ml of toluene. The organic phases are combined, dried over $MgSO_4$ and concentrated under reduced pressure. The crude product obtained is purified by chromatography on silica gel ($CH_2Cl_2$/MeOH, 95:5) to give 0.92 g (ρ=64%) of the compound of formula (9) in the form of a red-orange powder. The $^{31}$P NMR spectrum preserves, as expected, the ABCD spin system appearance, with slightly modified chemical shifts. $^{1}$H NMR ($CDCl_3$, 500 MHz, 300 K): δ (ppm) 6.45-8.42 (m, 45H), 5.75 (dd, 1H, $^3$J=10.5 Hz, $^2$J>1 Hz), 5.25 (dd, 1H, $^3$J=6.5 Hz, $^2$J=>1 Hz), 4.18, 4.16, 4.08, 4.02 (s, each 1H), 3.83 (s, 2H), 2.60 (t, 2H, $^3$J=3.5 Hz), 1.21-1.51 (m, 4H), 0.98, 0.15 (s, each 3H), 0.71 (s, 9H). $^{31}$P NMR ($CDCl_3$, 202.45 MHz, 300 K): δ (ppm) −30.2 (m, 2P), −33.8 (m, 2P). Calculated values: −29.9, −30.4, −33.7, −33.9 ppm. $^{13}$C NMR ($CDCl_3$, 125.75 MHz, 300 K): δ (ppm) 140.6 (s, 1C), 137 (s, 2C), 136.8 (s, 1C), 128.7 (s, 2C), 127.1-137.5 (m, 48C), 126.4 (s, 1C), 113.9 (s, 1C), 107.7, 106.2 (s, each 1C), 88.2 (m, 2C), 79.7 (m, 2C), 72.8, 72.6, 71.9, 71.3 (s, each 1C), 54.4 (s, 1C), 50.7 (s, 1C), 44.9 (s, 1C), 33.41, 30.7 (s, each 1C), 31.9 (s, 1C), 28.8, 27.5 (s, each 1C), 26.1 (s, 1C).

$C_{77}H_{76}P_4FeN$ (MW 1232.32, exact mass 1137.48): m/z 1194.425 $(M+Na)^+$; simulated 1194.428 (σ=0.048).

EXAMPLE 16

Synthesis of the Compound of Formula 10 with E=$(CH_2)_3$ and GF=4-Vinylbenzylamine A suspension of $FeCl_2$ (0.45 g, 3.54 mmol, 1 eq) in THF (20 ml) is admixed at −80° C. with a solution of 1,2-bis(diphenylphosphino)-4-tert-butylcyclopenta-dienyllithium (2.08 g, 3.48 mmol, 1 eq) in 30 ml of THF. The solution, held with stirring for 1 hour after return to ambient temperature, turns dark red. A solution of diisopropylphosphinocyclopentadienyllithium (0.65 g, 3.45 mmol, 1 eq) in 20 ml of THF is added at −80° C. Following return to ambient temperature, the dark red solution is taken to reflux for 4 hours. The solution is filtered over silica, concentrated under reduced pressure, and purified by chromatography on silica gel (eluent AcOEt/heptane, 1:3) to give 800 mg (ρ=30%) of 1,2-bis(diphenylphosphino)-1'-diisopropyl-phosphino-4-[4-(1,3-dioxan-2-yl)-2-methylbut-2-yl]butylferrocene in the form of an orange powder.

A solution of 1,2-bis(diphenylphosphino)-1'-diisopropylphosphino-4-[4-(1,3-dioxan-2-yl)-2-methylbut-2-yl]butylferrocene (1 g, 1.2 mmol) dissolved in 100 ml of THF is admixed with 15 ml of 2 N hydrochloric acid solution. After 2 hours with stirring at reflux, the reaction mixture is neutralized with saturated aqueous sodium hydrogencarbonate solution and extracted with 2×50 ml of $CH_2Cl_2$. The organic phase is dried over $MgSO_4$ and concentrated on a rotary evaporator. The crude product obtained is purified by chromatography on silica gel (eluent AcOEt/heptane 1:4) to give 630 mg (ρ=67%) of 1,2-bis(diphenylphosphino)-1'-diisopropylphosphino-4-(4-oxo-2-methylbut-2-yl)ferrocene in the form of a red powder.

A solution of $NaBH(OAc)_3$ (0.17 g, 0.8 mmol) and 4-vinylbenzylamine (0.26 g, 1.95 mmol) in 10 ml of dichloroethane is admixed dropwise at ambient temperature with a solution of 1,2-bis-(diphenylphosphino)-1'-diisopropylphosphino-4-(4-oxo-2-methylbut-2-yl)ferrocene (1.3 g, 1.2 mmol) in 5 ml of dichloroethane. The solution is held with stirring for 24 hours and then neutralized by addition of 1M aqueous sodium hydroxide solution. The aqueous phase is extracted with 2 times 30 ml of dichloromethane. The organic phases are combined, dried over $MgSO_4$, and concentrated under reduced pressure. The crude product obtained is purified by chromatography on silica gel ($CH_2Cl_2$/MeOH, 95:5) to give 0.4 g (ρ=55%) of 1,1',2-tris(diphenylphosphino)-2'-diisopropylphosphino-4-[2-methyl-5-(4-vinylbenzylamino)pent-2-yl]ferrocene in the form of a red-orange powder. The $^{31}$P NMR spectrum preserves, as expected, the $A_2B$ spin system appearance typical of these triphosphines, as described by Hierso et al. for the nonheterogeneizable analog in *Org. Lett.* 2004, 6, 3473-3476, with slightly modified chemical shifts.

$^{1}$H NMR ($CDCl_3$, 300 MHz, 303 K): δ (ppm) 6.85-7.70 (m, 24H), 6.69 (dd, 1H, $^3$J=17.7 Hz, $^3$J=10.8 Hz), 5.73 (dd, 1H, $^3$J=17.7 Hz, $^2$J=1.5 Hz), 5.24 (dd, 1H, $^3$J=10.8 Hz, $^2$J=1.5 Hz), 4.11 (m, 4H), 3.89 (m, 4H), 2.75 (m, 2H), 1.58 (m, 4H), 1.45 (hd, 2H, $^3J_{HH}$=6.9 Hz, $^2J_{HP}$=2.9 Hz), 1.30 (s, 6H), 0.84 (dd, 6H, $^3J_{HP}$=12.9 Hz, $^3J_{HH}$=6.9 Hz), 0.60 (s, 6H, $^3J_{HP}$=12.9 Hz, $^3J_{HH}$=6.9 Hz). $^{31}$P NMR ($CDCl_3$, 121.49 MHz, 303 K): δ (ppm) −3.4 (s, 1P), −25 (s, 2P). $^{13}$C NMR ($CDCl_3$, 75 MHz, 298 K): δ (ppm) 127.5-139 (m, 24C), 136.3 (s, 1C), 127.5 (s, 2C), 126.5 (s, 2C), 114.2 (s, 1C), 106.4 (s, 1C), 81.5 (d, 1C, $^1J_{CP}$=21 Hz), 81.5 (s, 1C), 80.5 (d, 1C, $^1J_{CP}$=21.7 Hz), 73.8, 73.7 (s, each 1C), 72.2, 71.3 (s, each 2C), 52.6 (s, 1C), 48.9 (s, 1C), 43.3 (d, 1C, $^{TS}J_{CP}$=3.7 Hz), 33.9 (s, 1C), 28.1 (d, 2C, $^{TS}J_{CP}$=3.7 Hz), 24.2 (m, 1C), 23.1 (d, 2C, $^1J_{CP}$=16 Hz), 20, 20.2 (d, each 2C, $^2J_{CP}$=14.3 Hz). $C_{55}H_{63}P_3FeN$ (MW 885.85, exact mass 885.34): m/z 886.349 $(M+H)^+$; simulated 886.351 (σ=0.574).

EXAMPLE 17

Immobilization of the Compound of Formula 10 with E=$(CH_2)_3$ and GF=4-Vinylbenzylamine on Polymeric Organic Support In a 500 ml Erlenmeyer flask, 4.5 g of gum Arabic and 2.8 g of sodium chloride and 112 ml of distilled water are taken to boiling. The solution is filtered on Célite® and 45 ml are introduced into a 100 ml reactor with plane-ground joints. Styrene (3.2 ml, 27.7 mmol), 1,1',2-tris(diphenylphosphino)-2'-diisopropylphosphino-4-[2-methyl-5-(4-vinylbenzylamino)pent-2-yl]ferrocene (0.4 g, 0.45 mmol), and divinylbenzene (0.41 g, 3.15 mmol) are dissolved in 3 ml of chlorobenzene. The monomer solution is injected into the surfactant solution with mechanical stirring. The mixture is heated to 85° C. and benzoyl peroxide (400 mg, 1.65 mmol) is added. After 20 hours at 85° C., the solution is filtered and the polymer is washed with 2×30 ml of hot water. The polymer is subsequently extracted with a Soxhlet apparatus in methanol for 24 hours, and then dried under vacuum to give 1.6 g of a polymeric ligand which is insoluble in organic solvents. The resin obtained is insoluble in all the usual organic solvents tested (THF, $CHCl_3$, $CH_2Cl_2$, toluene, $Et_2O$, ethyl acetate, hexane, methanol, DMF, DMSO, NMP, etc.). $^{31}P$ CP-MAS NMR analysis, obtained at a rotary speed of 14 Hz, shows the presence of a signal centered on −30 ppm. This shift is in agreement with the shift observed for the corresponding ligand in solution. Elemental analysis of this polymer showed a phosphorus content of 1.0%, which corresponds to a ligand charge of 0.0595 mmol/g.

EXAMPLE 18

Acylation Coupling Reaction of Phenylacetylene with Bromoacetophenone by the Compound of Formula (10) Supported on Polystyrene Resin This carbon-carbon coupling reaction was carried out under the following conditions of low metallic loads <1.0 mol %: a mixture of phenylacetylene (299 mg, 2.93 mmol, d=0.93), triethylamine (0.301 g, 2.93 mmol, d=0.726), bromoacetophenone (0.58 g, 2.95 mmol), the silica-supported ligand compound obtained from compound of formula (10) (0.24 g of polymer resin containing 0.0595 mmol/g of triphosphine ligand, or 0.0143 mmol), and the palladium precursor $[Pd(C_3H_5)Cl]_2$ (2.46 mg, 0.00715 mmol) is placed under argon in a Schlenk tube. 2 ml of DMF, distilled and degassed by sparging with nitrogen, is added, and the mixture is held at 120° C. for 20 hours. The cooled mixture is filtered to recover the ligand compound and the metal (less than 1 ppb of Pd, by ICP analysis, remaining in solution). The filtrate is evaporated to dryness under vacuum, and the residue is dissolved in 10 ml of ethyl ether with 10 ml of water for extraction. The organic phases are dried over magnesium sulfate. GC analysis beforehand indicates total conversion of the bromoacetophenone into coupling product, for a 95% yield after evaporation of the solvent and chromatographic treatment. The catalyst isolated by filtration is reused in reaction according to the same procedure. GC analysis again shows total conversion of the bromoacetophenone into coupling product, which is obtained with a 95% yield after evaporation of the solvent and chromatographic treatment. The isolated catalyst can be reused in this way a number of times (six times) with no significant drop in activity, the limitation lying in the losses during filtration.

EXAMPLE 19

Generic Synthesis of the Compounds of Formula (11) to (16)

A suspension of $FeCl_2$ (1 eq) in THF (45 ml/g) is admixed at −80° C. with a solution of 1,2-bis(diphenylphosphino)-4-tert-butylcyclopentadienyl-lithium (1 eq) in THF (15 ml/g). The solution, held with stirring for 1 hour after return to ambient temperature, turns dark red. A solution of the appropriate cyclopentadienyllithium (1 eq) in THF (30 ml/g) is added at −80° C. Following return to ambient temperature, the dark red solution is taken to reflux for 4 hours. The solution is filtered over silica, concentrated under reduced pressure, and purified by chromatography on silica gel to give the corresponding ferrocenyl ligand. The chemical shifts and the characterizations correspond to the data for the analogous non-heterogeneizable compounds as described by Broussier et al. in *J. Organomet. Chem.* 2000, 598, 365-373.

EXAMPLE 20

Generic Synthesis of the Compounds of Formula (17) to (18)

A suspension of $FeCl_2$ (1 eq) in THF (45 ml/g) is admixed at −80° C. with a solution of 1-(diphenylphosphino)-4-tert-butylcyclopentadienyl-lithium (1 eq) in THF (15 ml/g). The solution, held with stirring for 1 hour after return to ambient temperature, turns dark red. A solution of the appropriate cyclopentadienyllithium (1 eq) in THF (30 ml/g) is added at −80° C. Following return to ambient temperature, the dark red solution is taken to reflux for 4 hours. The solution is filtered over silica, concentrated under reduced pressure, and purified by chromatography on silica gel to give the corresponding ferrocenyl ligand. The chemical shifts and the characterizations correspond to the data for the analogous non-heterogeneizable compounds as described by Broussier et al. in *J. Organomet. Chem.* 2000, 598, 365-373.

In conclusion, in the context of sustainable chemistry, resource economy, and in particular the most rare species, such as precious metals, high-performance catalytic systems which operate with amounts of catalyst of 0.1 to 0.0001 mol % in relation to the substrate have been developed for a number of years with ferrocenyl polyphosphine ligands, in particular of formulae (a) to (l).

With the invention, the use of these catalytic systems of formulae (a) to (l), but in supported and recoverable form, enables even further improvement in the "green chemistry" aspects, by the recovery of the metals and the ease of separation of the products formed and the catalyst, even when used in a higher amount but below 1 mol % of catalyst.

The immobilization of these ligands allows an increase in the local density of coordinating atoms on a solid support, by the controlled implantation of 3 to 4 phosphorus atoms within a radius of 3 to 5 angstroms. These immobilized ligands of polyphosorated resin type, and particularly for tetraphosphines (4 phosphorus atoms constrained in a great proximity), have never, to the knowledge of the inventors, been synthesized before. Their utility in catalysis has been demonstrated experimentally in cross-coupling.

Moreover, on the basis of these new, heterogeneizable phosphinyl ligands, it is possible to gain access both to purely heterogeneous (insoluble) resins and to polymeric resins which are soluble selectively according to the solvents chosen.

The concept of immobilization of these supports has been validated through original synthesis of the target ligands, making it possible, on the one hand, to introduce a functional group which serves as an anchor point for their fixation on a solid support, and on the other hand to conserve the special conformation of these ligands, as verified by X-ray diffraction and by the specific spin systems observed in $^{31}P$ NMR.

This conformation, due to the presence of sterically hindering groups attached directly to the cyclopentadienes, was conserved by introducing gem dimethyl groups, which mimic the presence of a tert-butyl group. $^{31}P$ NMR of the various heterogeneizable ligands formed, and also the study of these ligands by X-ray diffraction for some of them, enable the success of this strategy to be confirmed.

The invention claimed is:

1. A compound of formula (I) below:

Formula (I)

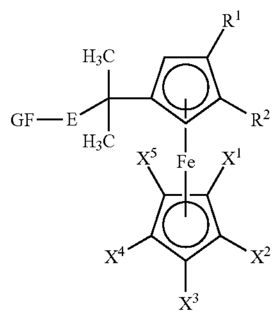

wherein:

E is a saturated or unsaturated, linear or branched $C_1$ to $C_{30}$, alkyl chain which optionally comprises at least one heteroatom, GF is a reactive group of vinyl; formyl; carbonyl; acetal; styrenyl; alcohol; silane; alkoxysilane in which the alkoxy chain is a saturated or unsaturated, linear or branched $C_1$ to $C_{30}$ chain optionally comprising at least one heteroatom, silanol; siloxane; amine; imine; amide; thiol; or carboxyl, and from the groups of the following formulae:

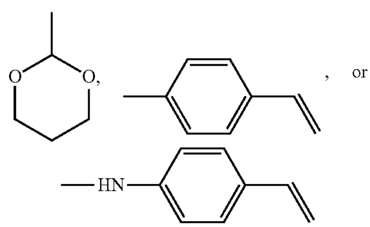

$R^1$ is a phosphine group $P(R^4)_2$, $R^2$ is H or a phosphine group $P(R^6)_2$, $X^1$, $X^2$, $X^3$, and $X^4$ are identical or different and are selected independently of one another from a hydrogen atom, a group $P(R^8)_2$, a group $—C(CH_3)_2—P(R^3)_2$, or an amino group $R^7N(R^5)_2$, $X^5$ is either a group GF-E-$C(CH_3)_2$— in which GF and E are identical to GF and E defined above, or H, or a phosphine group $P(R^{10})_2$ or an amino group $R^{11}N(R^9)_2$, $R^3$, $R^4$, $R^5$, $R^6$, $R^7$, $R^8$, $R^9$, $R^{10}$ and $R^{11}$ are, independently of one another, selected from a saturated or unsaturated, linear or branched $C_1$ to $C_{30}$ alkyl group comprising optionally at least one heteroatom, or a $C_3$ to $C_7$ aryl, or cyclic or acyclic aliphatic group, optionally comprising a heteroatom, and optionally substituted.

2. The compound of claim 1, wherein in the formula (I) $X^5$ is GF-E-$C(CH_3)_2$—, $X^1$ and $X^4$ are H, and in that they have the formula (I-A) below:

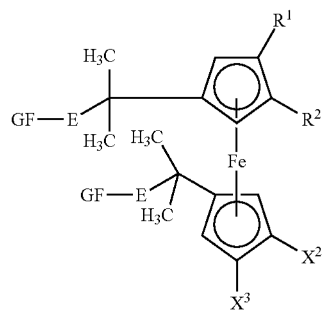

3. The compound of claim 2, wherein formula (I) and (I-A) include $X^2$=$X^3$=$P(Ph)_2$, $X^1$ and $X^4$ are H and $R^1$=$R^2$=$P(Ph)_2$, and in that they have a formulae (1) to (8) below, giving a symmetrical compound:

Formula (1)

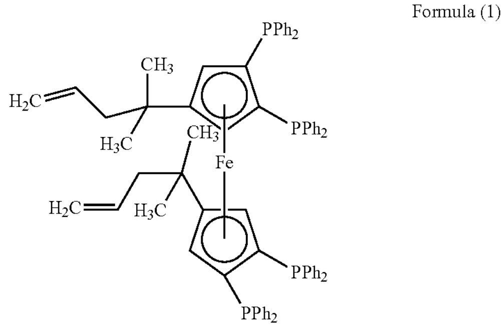

Formula (2)

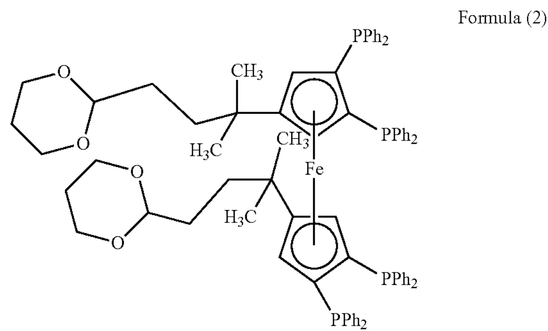

-continued

Formula (3)

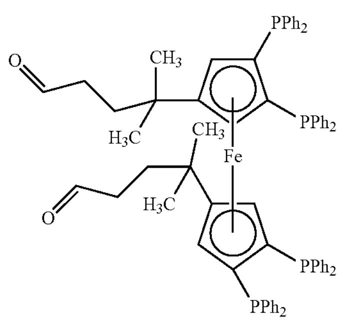

Formula (4)

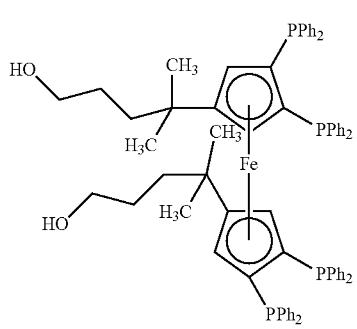

Formula (5)

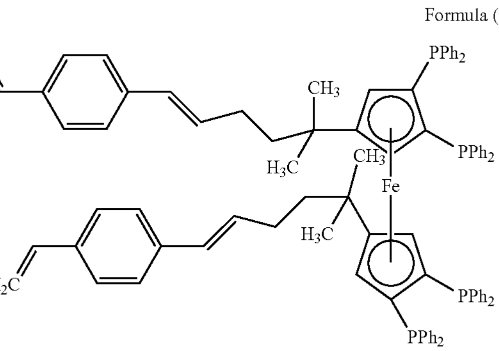

Formula (6)

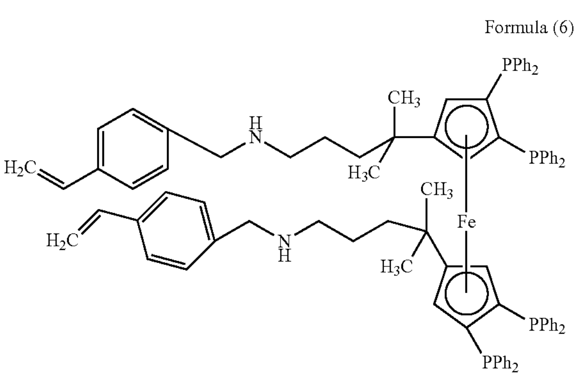

-continued

Formula (7)

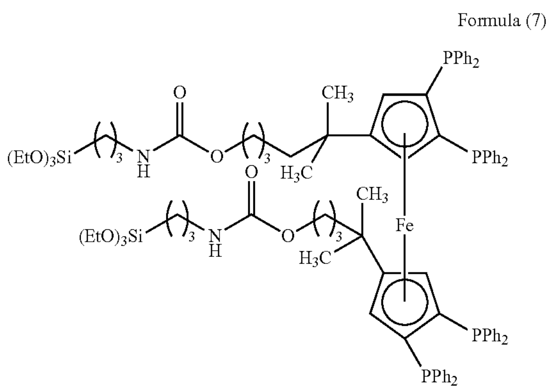

Formula (8)

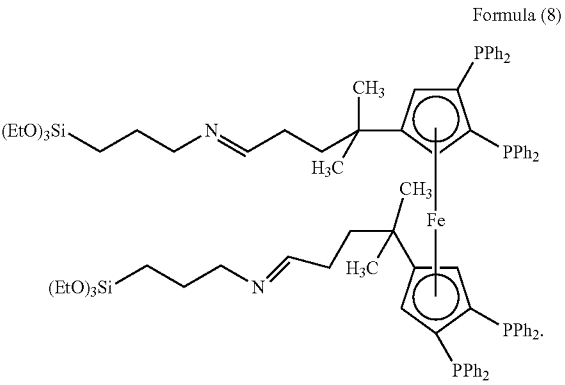

4. The compound of claim 1, wherein:

$X^5$ is different from GF-E-$C(CH_3)_2$, making them asymmetrical, and in that they have the formulae (9) to (18) below, wherein:

$R^4$ and $R^6$ denote, independently of one another, an isopropyl, cyclohexyl, tert-butyl, or phenyl, or furyl, group, which are optionally substituted, or a $CF_3$ group, $R^5$ denotes:

either a saturated or unsaturated, linear or branched $C_1$ to $C_{30}$ alkyl chain which may comprise at least one heteroatom, or a $C_3$ to $C_7$ aryl, or acyclic or cyclic aliphatic, group, optionally comprising a heteroatom and optionally substituted, or a $CF_3$ group, and in that they have a formulae (9) to (18) below:

Formula (9)

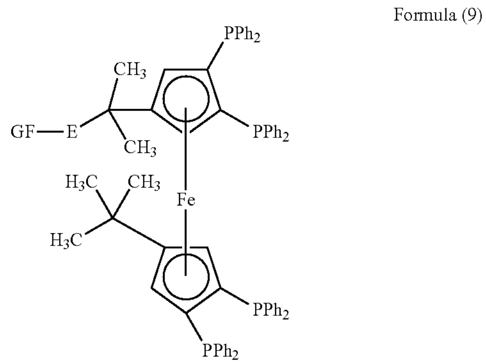

-continued

Formula (10)

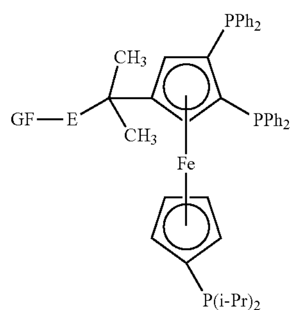

Formula (11)

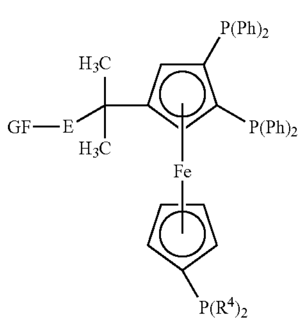

Formula (12)

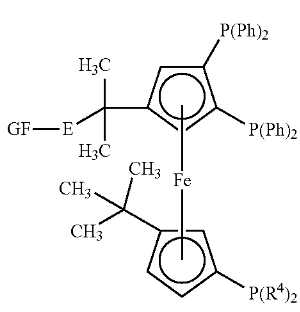

Formula (13)

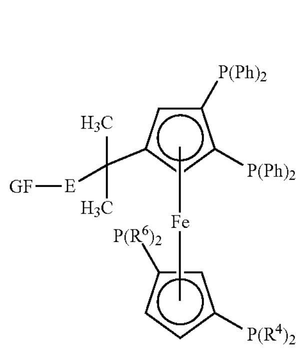

Formula (14)

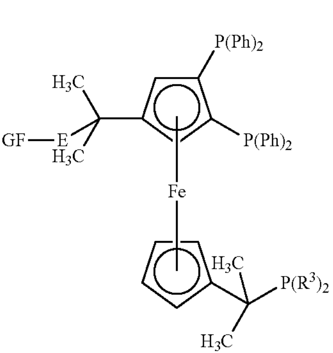

-continued

Formula (15)

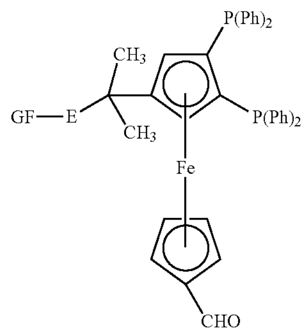

Formula (16)

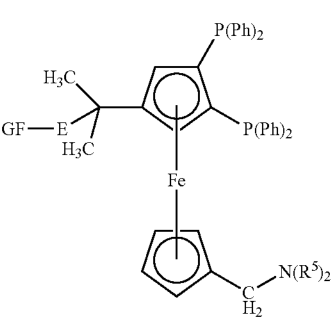

Formula (17)

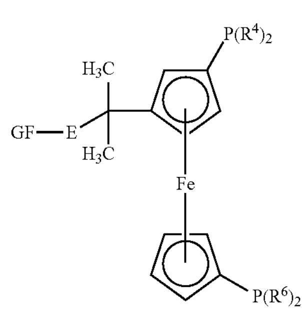

Formula (18)

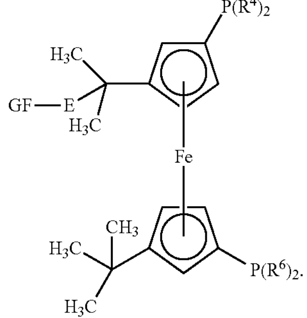

5. A complex wherein the complex comprises a compound of claim 1, which is complexed with a metal selected from transition metals.

6. A supported complex wherein the supported complex comprises a complex of claim 5, immobilized on a support by grafting or polymerization of the reactive group GF with a reactive group of a support.

7. A supported ligand wherein the supported ligand comprises a compound of claim 1, immobilized by grafting or polymerization of its one or more reactive groups GF with one or more reactive groups of a support.

8. A complex wherein the complex comprises a compound of claim 3, which is complexed with a metal selected from transition metals.

9. A supported complex wherein the supported complex comprises a complex of claim 8, immobilized on a support by grafting or polymerization of the reactive group GF with a reactive group of a support.

10. A supported ligand wherein the supported ligand comprises a compound of claim 3 immobilized by grafting or polymerization of its one or more reactive groups GF with one or more reactive groups of a support.

11. The compound according to claim 1, wherein:

E is a saturated or unsaturated, linear or branched $C_1$ to $C_{10}$ alkyl chain which optionally comprises at least one heteroatom, GF is a reactive group of: vinyl; formyl; carbonyl; acetal; styrenyl; alcohol; silane; alkoxysilane in which the alkoxy chain is a saturated or unsaturated, linear or branched $C_1$ to $C_{10}$ chain optionally comprising at least one heteroatom; silanol; siloxane; amine; imine; amide; thiol; or carboxyl, and from the groups of the following formulae:

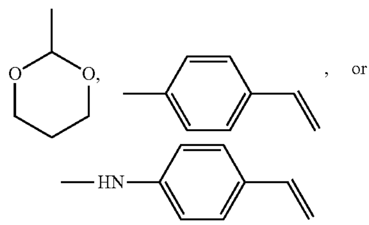

$R^1$ is a phosphine group $P(R^4)_2$, $R^2$ is H or a phosphine group $P(R^6)_2$, $X^1$, $X^2$, $X^3$, and $X^4$ are identical or different and are selected independently of one another from a hydrogen atom, a group $P(R^8)_2$, a group —$C(CH_3)_2$—$P(R^3)_2$, or an amino group $R^7N(R^5)_2$, $X^5$ is either a group GF-E-$C(CH_3)_2$— in which GF and E are identical to GF and E defined above, or H, or a phosphine group $P(R^{10})_2$or an amino group $R^{11}N(R^9)_2$, $R^3$, $R^4$, $R^5$, $R^6$, $R^7$, $R^8$, $R^9$, $R^{10}$ and $R^{11}$ are independently of one another, selected from a saturated or unsaturated, linear or branched $C_1$ to $C_{10}$ alkyl group comprising optionally at least one heteroatom, or a $C_3$ to $C_7$ aryl, or cyclic or acyclic aliphatic group, optionally comprising a heteroatom, and optionally substituted.

12. The compound of claim 11, wherein the formula (I):

$X^5$ is different from GF-E-$C(CH_3)_2$, making them asymmetrical, and in that they have the formulae (9) to (18) below, wherein:

$R^4$ and $R^6$ denote, independently of one another, an isopropyl, cyclohexyl, tert-butyl, or phenyl, or furyl, group, which are optionally substituted by at least one methyl or methoxy group, a halogen atom, or a $CF_3$ group, $R^5$ denotes:

either a saturated or unsaturated, linear or branched $C_3$ to $C_{10}$ alkyl chain which may comprise at least one heteroatom, or a $C_3$ to $C_7$ aryl, or acyclic or cyclic aliphatic group, optionally comprising a heteroatom and optionally substituted by at least one methyl or methoxy group, a halogen atom or a $CF_3$ group, and in that they have a formulae (9) to (18) below:

Formula (9)

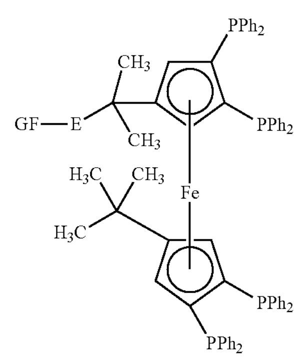

Formula (10)

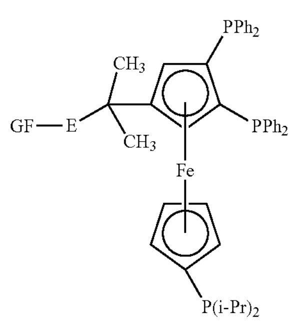

Formula (11)

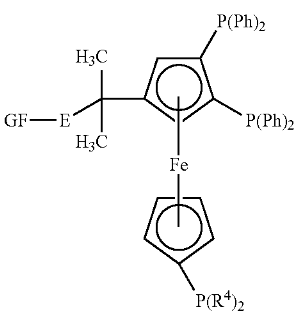

Formula (12)

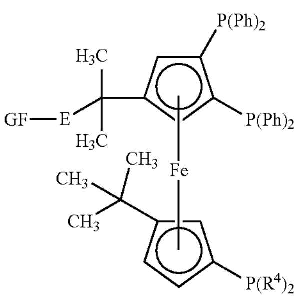

Formula (13)

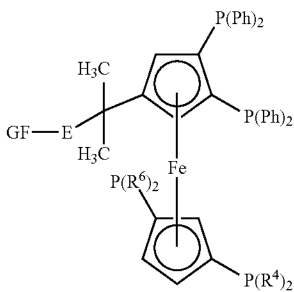

-continued

Formula (14)

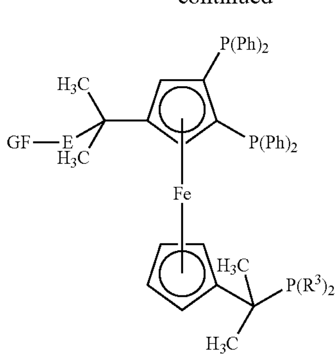

Formula (15)

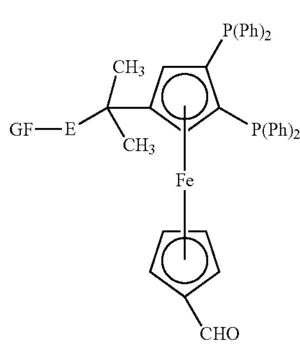

Formula (16)

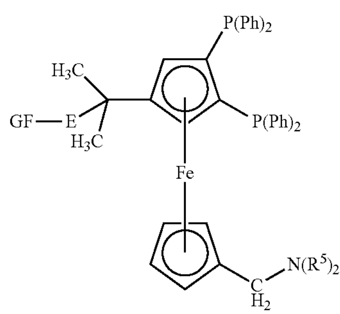

Formula (17)

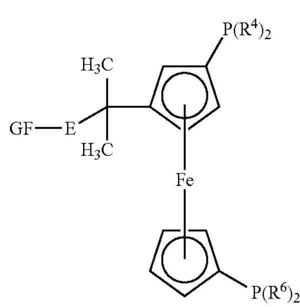

Formula (18)

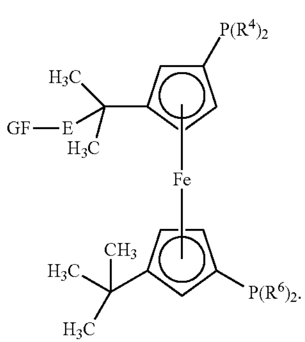

13. A complex wherein the complex comprises a compound according to claim 12, which is complexed with a metal selected from transition metals.

14. A supported complex wherein the supported complex comprises a complex of claim 13, immobilized on a support by grafting or polymerization of the reactive group GF with a reactive group of a support.

15. A supported ligand wherein the supported ligand comprises a compound of claim 12, immobilized by grafting or polymerization of its one or more reactive groups GF with one or more reactive groups of a support.

16. The compound of claim 1, wherein

E is a saturated or unsaturated, linear or branched $C_1$ to $C_5$ alkyl chain which optionally comprises at least one heteroatom, GF is a reactive group of: vinyl; formyl; carbonyl; acetal; styrenyl; alcohol; silane; alkoxysilane in which the alkoxy chain is a saturated or unsaturated, linear or branched C1 to C5 chain optionally comprising at least one heteroatom; silanol; siloxane; amine; imine; amide; thiol; or carboxyl, and from the groups of the following formulae:

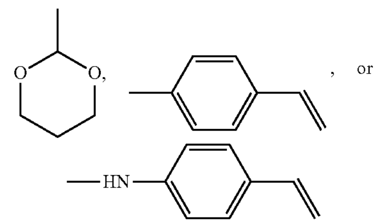

$R^1$ is a phosphine group $P(R^4)_2$, $R^2$ is H or a phosphine group $P(R^6)_2$, $X^1$, $X^2$, $X^3$, and $X^4$ are identical or different and are selected independently of one another from a hydrogen atom, a group $P(R^8)_2$, a group $—C(CH_3)_2—P(R^3)_2$, or an amino group $R^7N(R^5)_2$, $X^5$ is either a group GF-E-$C(CH_3)_2$— in which GF and E are identical to GF and E defined above, or H, or a phosphine group $P(R_{10})_2$ or an amino group $R_{11}N(R_9)_2$, $R^3$, $R^4$, $R^5$, $R^6$, $R^7$, $R^8$, $R^9$, $R^{10}$ and $R^{11}$ are independently of one another, selected from a saturated or unsaturated, linear or branched $C_1$ to $C_5$ alkyl group comprising optionally at least one heteroatom, or a $C_3$ to $C_7$ aryl, or cyclic or acyclic aliphatic group, optionally comprising a heteroatom, and optionally substituted.

17. A complex wherein the complex comprises a compound according to claim 16, which is complexed with a metal selected from a transition metal.

18. A supported complex wherein the supported complex comprises a complex according to claim 17, immobilized on a support by grafting or polymerization of the reactive group GF with the reactive group of a support.

19. A supported ligand wherein the supported complex comprises a compound of claim 16, immobilized by grafting or polymerization of its one or more reactive groups GF with one or more reactive group of a support.

20. The compound of claim 1, wherein:

in E, GF, $R^3$, $R^4$, $R^5$, $R^6$, $R^7$, $R^8$, $R^9$, $R^{10}$, the optionally at least one heteroatom is N and/or O, and when in $R^3$, $R^4$, $R^5$, $R^6$, $R^7$, $R^8$, $R^9$, $R^{10}$ and $R^{11}$ are groups which are substituted, then these groups are substituted by at least one methyl, methoxy or halogen, or $CF_3$ group.

21. A complex wherein the complex comprises a compound of claim 20, which is complexed with a metal selected from transition metals.

22. A supported complex wherein the supported complex comprises a complex of claim 21, immobilized on a support by grafting or polymerization of the reactive group GF with a reactive group of a support.

23. A supported ligand wherein the supported ligand comprises a compound of claim 20, immobilized by grafting or polymerization of its one or more reactive groups GF with one or more reactive group of a support.

24. The compound according to claim 1:

wherein $R^3$, $R^4$, $R^5$, $R^6$, $R^7$, $R^8$, $R^9$, $R^{10}$, and $R^{11}$ are selected from a —$CH_2$— group, ethyl (Et), isopropyl (i-Pr), cyclohexyl (Cy), tert-butyl (t-Bu), or phenyl (Ph), or furyl (Fu), which are optionally substituted by at least one methyl, methoxy, halogen, or $CF_3$ group.

25. A complex wherein the complex comprises a compound of claim 24, which is complexed with a metal selected from transition metals.

26. A supported complex wherein the supported complex comprises a complex of claim 25, immobilized on a support by grafting or polymerization of the reactive group GF with a reactive group of a support.

27. A supported ligand wherein the supported ligand comprises a compound of claim 24, immobilized by grafting or polymerization of its one or more reactive groups GF with one or more reactive group of a support.

28. The compound according to claim 1:

wherein $R^3$, $R^4$, $R^6$, $R^8$, and $R^{10}$ are a phenyl group, $R^5$ and $R^9$ are both an ethyl group, and $R^7$ and $R^{11}$ are both a —$CH_2$— group.

29. A complex wherein the complex comprises a compound of claim 28, which is complexed with a metal selected from transition metals.

30. A supported complex wherein the supported complex comprises a complex of claim 29, immobilized on a support by grafting or polymerization of the reactive group GF with a reactive group of a support.

31. A supported ligand wherein the supported ligand comprises a compound of claim 24, immobilized by grafting or polymerization of its one or more reactive groups GF with one or more reactive group of a support.

* * * * *